US 12,097,294 B2

(12) United States Patent
Strader et al.

(10) Patent No.: US 12,097,294 B2
(45) Date of Patent: *Sep. 24, 2024

(54) TRANSDERMAL PATCH WITH SEPARATED REGIONS FOR DELIVERY OF IMMUNOMODULATORS

(71) Applicant: Avrio Genetics LLC, Allentown, PA (US)

(72) Inventors: James Strader, Austin, TX (US); Jovan Hutton Pulitzer, Frisco, TX (US)

(73) Assignee: Avrio Genetics LLC, Allentown, PA (US)

( * ) Notice: Subject to any disclaimer, the term of this patent is extended or adjusted under 35 U.S.C. 154(b) by 284 days.

This patent is subject to a terminal disclaimer.

(21) Appl. No.: 17/851,743

(22) Filed: Jun. 28, 2022

(65) Prior Publication Data
US 2023/0042512 A1     Feb. 9, 2023

Related U.S. Application Data

(63) Continuation of application No. 15/865,001, filed on Jan. 8, 2018, now Pat. No. 11,369,576.
(Continued)

(51) Int. Cl.
*A61K 9/70* (2006.01)
*A61K 9/06* (2006.01)
(Continued)

(52) U.S. Cl.
CPC .............. *A61K 9/7092* (2013.01); *A61K 9/06* (2013.01); *A61K 9/7084* (2013.01);
(Continued)

(58) Field of Classification Search
CPC ...... A61K 9/7092; A61K 9/06; A61K 9/7084; A61K 31/4188; A61K 31/437;
(Continued)

(56) References Cited

U.S. PATENT DOCUMENTS

| 4,573,996 A | 3/1986 | Kwiatek et al. |
| 4,666,441 A | 5/1987 | Andriola et al. |

(Continued)

OTHER PUBLICATIONS

Baumann L.S. et al., "Lip Silicone Granulomatous Foreign Body Reaction Treaded with Aldara (Imiquimod 5%)", Dermatologic Surgery Apr. 1, 2003 US, vol. 29, No. 4, Apr. 1, 2003 (Apr. 1, 2003), pp. 429-432, XP002745005, ISSN: 1076-0512, p. 429, left-hand column, paragraph middle. Apr. 1, 2003.

(Continued)

*Primary Examiner* — Trevor Love

(57) ABSTRACT

A method for creating a consolidated compound for delivering an immunomodulatory and imiquimod to a patient, comprising diluting immunomodulator extract to a desired dilution by transferring a desired quantity of the concentrated immunomodulator to an associated sterile container, the associated sterile container having a defined volume of diluted immunomodulator after dilution thereof, providing a viscous encapsulation material, selecting a prescribed amount of concentrated immunomodulator, the prescribed amount defined as that amount of the diluted immunomodulator extract required to provide a number of doses equal to the number of dispensable increments from the container containing the viscous encapsulation material, introducing the selected amount of each of the diluted immunomodulator extract into the viscous encapsulation material, introducing an amount of imiquimod into the viscous encapsulation material, and mixing the introduced amount of each of the diluted immunomodulator extracts and the introduced amount of imiquimod with the viscous encapsulating material.

3 Claims, 30 Drawing Sheets

Related U.S. Application Data

(60) Provisional application No. 62/443,441, filed on Jan. 6, 2017, provisional application No. 62/443,429, filed on Jan. 6, 2017, provisional application No. 62/443,433, filed on Jan. 6, 2017, provisional application No. 62/443,390, filed on Jan. 6, 2017.

(51) Int. Cl.

| | | |
|---|---|---|
| *A61K 31/4188* | (2006.01) | |
| *A61K 31/437* | (2006.01) | |
| *A61K 39/00* | (2006.01) | |
| *A61K 39/35* | (2006.01) | |
| *A61K 39/36* | (2006.01) | |
| *A61K 45/06* | (2006.01) | |
| *A61P 17/00* | (2006.01) | |
| *A61P 37/02* | (2006.01) | |
| *A61P 37/08* | (2006.01) | |
| *A61K 47/10* | (2017.01) | |
| *A61K 47/12* | (2006.01) | |

(52) U.S. Cl.
CPC ........ *A61K 31/4188* (2013.01); *A61K 31/437* (2013.01); *A61K 39/0008* (2013.01); *A61K 39/35* (2013.01); *A61K 39/36* (2013.01); *A61K 45/06* (2013.01); *A61P 17/00* (2018.01); *A61P 37/02* (2018.01); *A61P 37/08* (2018.01); *A61K 9/703* (2013.01); *A61K 2039/54* (2013.01); *A61K 47/10* (2013.01); *A61K 47/12* (2013.01)

(58) Field of Classification Search
CPC .... A61K 39/0008; A61K 39/35; A61K 39/36; A61K 45/06; A61P 17/00; A61P 37/02; A61P 37/08

See application file for complete search history.

(56) References Cited

U.S. PATENT DOCUMENTS

| | | |
|---|---|---|
| 4,887,611 A | 12/1989 | Rudiger et al. |
| 5,462,743 A | 10/1995 | Turner et al. |
| 6,488,937 B1 | 12/2002 | Smits |
| 2003/0082212 A1 | 5/2003 | Smits |
| 2006/0020514 A1 | 1/2006 | Yered |
| 2006/0212318 A1 | 9/2006 | Dooley et al. |
| 2009/0169602 A1 | 7/2009 | Senti et al. |
| 2014/0220056 A1 | 8/2014 | Shishido et al. |
| 2015/0290129 A1 | 10/2015 | Strader et al. |

OTHER PUBLICATIONS

Cox et al., J. Allergy Clin. Immunol. 2011; 127(1):S1-S55 Jan. 1, 2011.

E. Alvarez-Cuesta et al., "Subcutaneous immunotherapy", Allergy, vol. 61, No. s82, Oct. 2006 (Oct. 2006), pp. 5-13, XP055319495, UK Oct. 1, 2006.

El Maghraby et al. Eur. J. Pharma. Sci. 2008; 34:203-222 Apr. 18, 2008.

PCT: European Patent Office Searching Authority, International Search Report and Written Opinion of PCT/IB2015/001330 (related application), Oct. 5, 2015, 14 pgs. Oct. 5, 2015.

PCT: European Patent Office Searching Authority, International Search Report and Written Opinion of PCT/IB2016/001332 (related application), Nov. 24, 2016, 13 pgs. Nov. 24, 2016.

Prieto-Garcia Alicia et al: "Autoimmune Progesterone Dermatitis: Clinical Presentation and Management with Progesterone Desensitization for Successful In Vitro Fertilization", Fertility and Sterility, vol. 95, No. 3, Mar. 2011 (Mar. 2011), pp. 1121.e9-1121.e13, XP28147753, p. 1121.e9, left-hand column p. 1121.e12, left-hand column, paragraph top Mar. 1, 2001.

702 — LIQUID ANTIGEN OR COMBINATION OF ANTIGENS SUSPENDED IN STERILE AGENT (FROM VENDOR)

710 — STERILE VISCOUS ENCAPSULATION AND CONTAINMENT MATERIAL

704 — ANTIGEN DILUTION

706 — COMBINATION

712 — COMBINED ANTIGEN (DILUTED)/ENCAPSULATION STORAGE

COMBINED ANTIGEN (DILUTED)/ENCAPSULATION TO MEDICAL PROFESSIONAL FOR MANAGEMENT AND DISPOSITION

FIG. 7

802 — CAT → → → → → C 810, C 812

804 — DOG → → → D 814 → → D 816

806 — POLLEN → → → → P 818 → P 820

FIG. 8

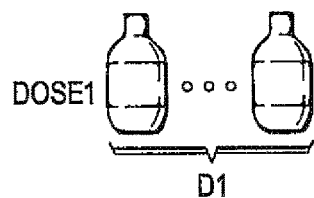
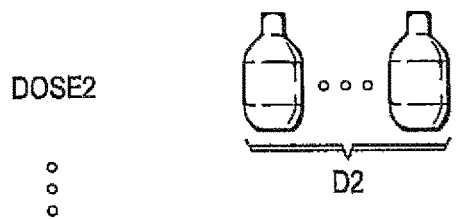
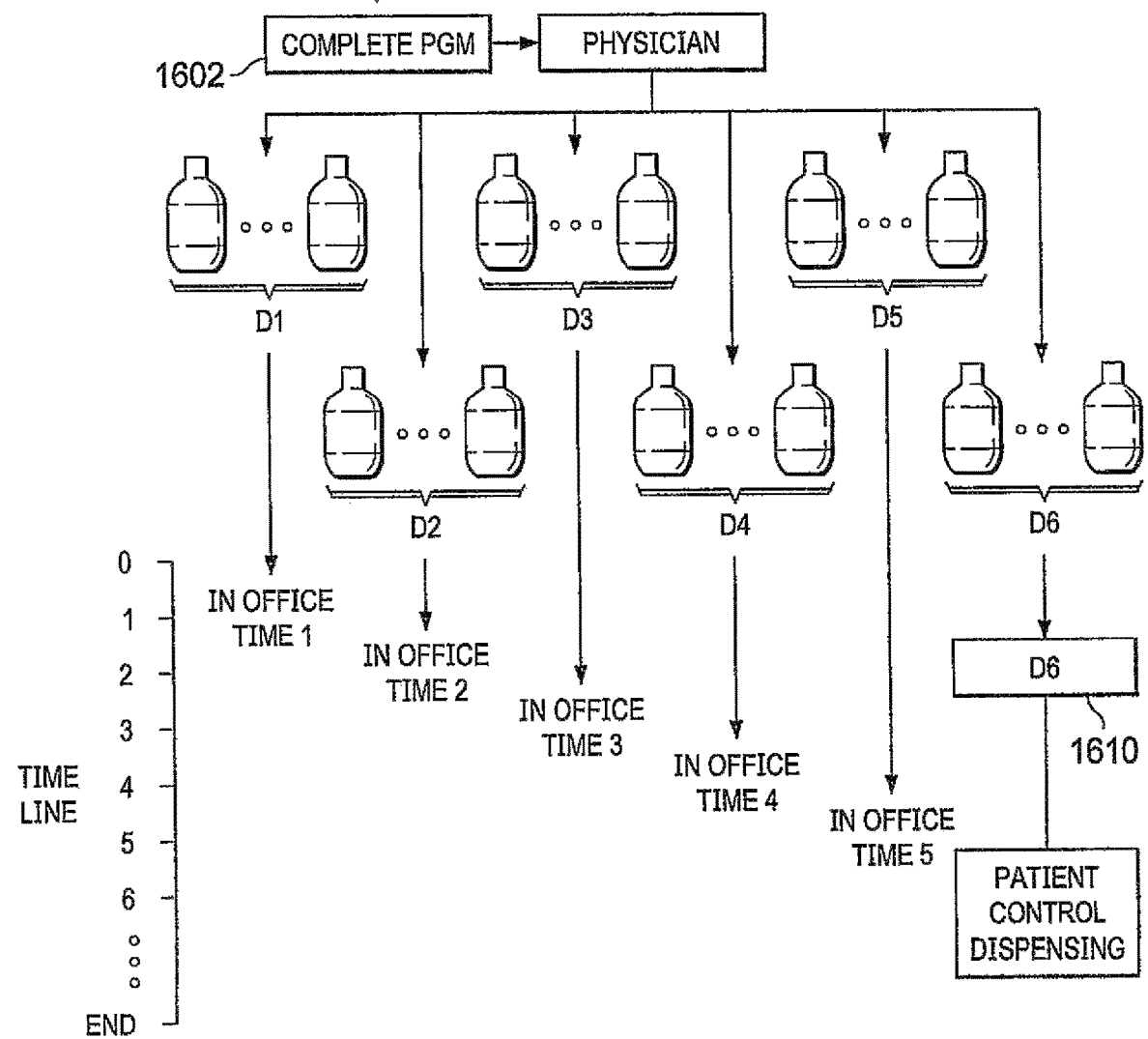
FIG. 16

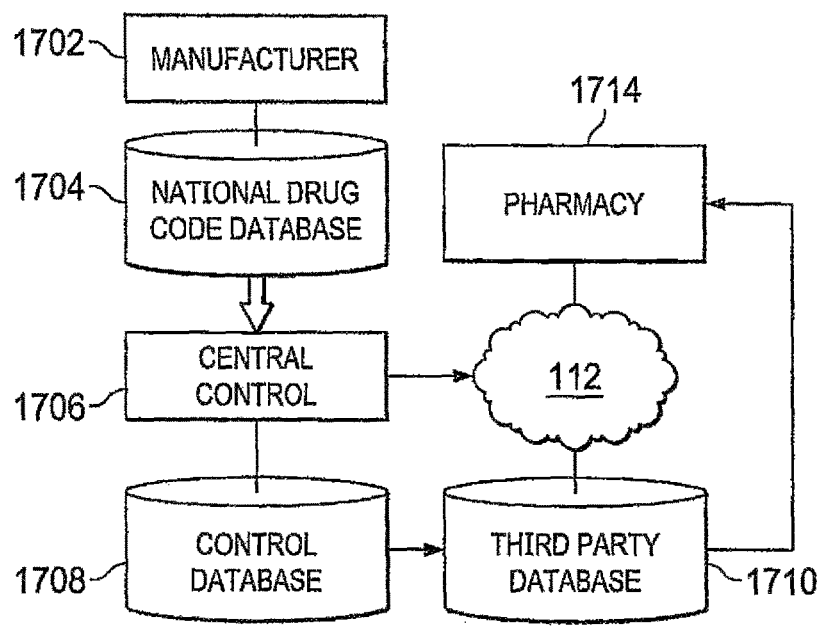
FIG. 17
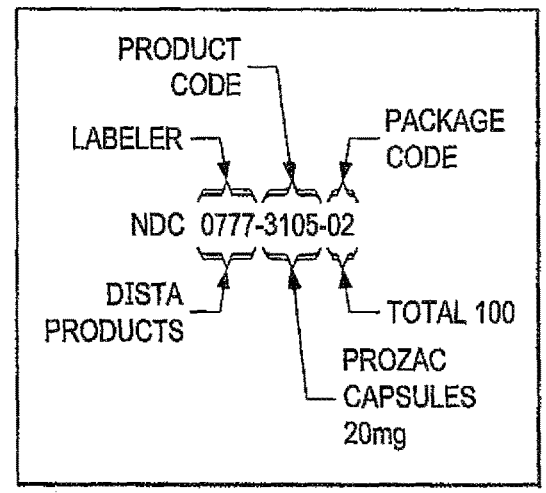
FIG. 17A
| THIRD PARTY DATABASE | | | |
|---|---|---|---|
| NATIONAL DRUG CODE | AVERAGE WHOLESALE PRICE | INFORMATION | |
| XX.XX | $4.44 | AAA | |
| YY.YY | $5.44 | BBB | |
| ZZ.ZZ | $6.44 | CCC | |
| | | | |
FIG. 18

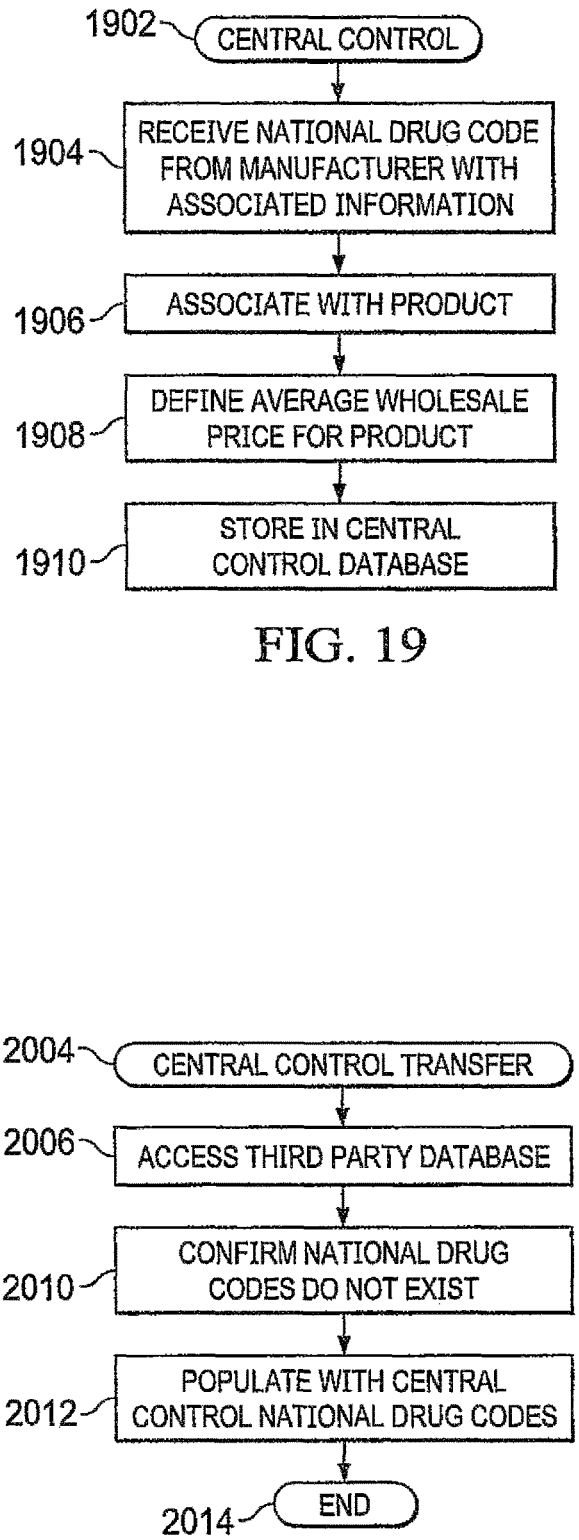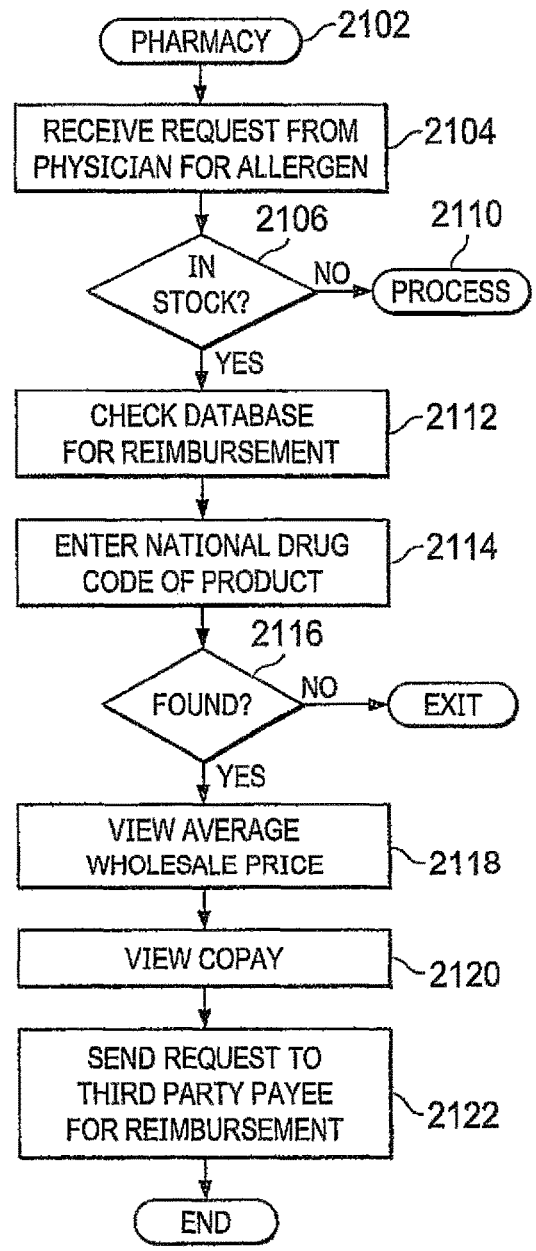
FIG. 19
FIG. 20
FIG. 21

| SINGLE ANTIGEN TABLE | | | | | | | | |
|---|---|---|---|---|---|---|---|---|
| NDC | ANTIGEN | DILUTION PROCEDURE | D1 (BASE) | D2 | D3 | D4 | D5 | D6 |
| XXX | CAT | STANDARD | X1 | X2 | X3 | X4 | X5 | X6 |
| | | | Y1 | Y2 | Y3 | Y4 | Y5 | Y6 |
| | | | Z1 | Z2 | Z3 | Z4 | Z5 | Z6 |
| ⋮ | ⋮ | ⋮ | ⋮ | ⋮ | ⋮ | ⋮ | ⋮ | ⋮ |
| YYY | DOG | STANDARD | X1 | X2 | X3 | X4 | X5 | X6 |
| | | | Y1 | Y2 | Y3 | Y4 | Y5 | Y6 |
| | | | Z1 | Z2 | Z3 | Z4 | Z5 | Z6 |
| ⋮ | ⋮ | ⋮ | ⋮ | ⋮ | ⋮ | ⋮ | ⋮ | ⋮ |

FIG. 27

| DILUTION PROCEDURE | D1 | D2 | D3 | D4 | D5 | D6 |
|---|---|---|---|---|---|---|
| S1 | Z1 | Z2 | Z3 | Z4 | Z5 | Z6 |
| S2 | Z1' | Z2' | Z3' | Z4' | Z5' | Z6' |
| S3 | Z1" | Z2" | Z3" | Z4" | Z5" | Z6" |

FIG. 27A

TRANSDERMAL PATCH WITH SEPARATED REGIONS FOR DELIVERY OF IMMUNOMODULATORS

CROSS-REFERENCE TO RELATED APPLICATIONS

This application is a Continuation of U.S. application Ser. No. 15/865,001, filed Jan. 8, 2018, entitled TRANSDERMAL PATCH WITH SEPARATED REGIONS FOR DELIVERY OF IMMUNOMODULATORS, issued as U.S. Pat. No. 11,369,576 on Jun. 28, 2022, which claims the benefit of U.S. Provisional Application No. 62/443,429, filed on Jan. 6, 2017, entitled TRANSDERMAL CREAM CONTAINING IMMUNOMODULATORS AND IMIQUIMOD. This application also claims the benefit of U.S. Provisional Application No. 62/443,390, filed on Jan. 6, 2017, entitled METHOD FOR DELIVERY OF IMMUNOMODULATORS AND IMIQUIMOD TO A PATIENT. This application also claims the benefit of U.S. Provisional Application No. 62/443,433, filed Jan. 6, 2017, entitled METHOD FOR DELIVERY OF A MAINTENANCE DOSE OF IMMUNOMODULATORS TO A PATIENT. This application also claims the benefit of U.S. Provisional Application No. 62/443,441, filed on Jan. 6, 2017, entitled METHOD FOR DELIVERY OF A MAINTENANCE DOSE OF IMMUNOMODULATORS AND IMIQUIMOD TO A PATIENT. Application Nos. 62/443,429, 62/443,390, 62/443,433, and 62/443,441 are herein incorporated by reference in their entirety.

TECHNICAL FIELD

This application relates to the delivery of immunomodulators to a patient and, more particularly, to the use of carriers for the dispensing of such across the dermis of the patient.

BACKGROUND

Immunotherapy (IT) is recognized as most curative treatment for allergies. By exposing the immune system to slowly increasing concentrations of immunomodulators such as an allergen or antigen, it will eventually stabilize and regain control the portion that is hypersensitive to the allergen or antigen. In general, immunotherapy is the "treatment of disease by inducing, enhancing, or suppressing an immune response." Immunotherapies designed to elicit or amplify an immune response are classified as activation immunotherapies, while immunotherapies that reduce or suppress are classified as suppression immunotherapies. The active agents of immunotherapy are collectively called immunomodulators. They are a diverse array of recombinant, synthetic and natural preparations, often cytokines.

Immunotherapy involved in the treatment of allergies is a type of suppression immunotherapy, often termed desensitization or hypo-sensitization. This is compared with allergy treatments such as antihistamines or corticosteroids which treat only the symptoms of allergic disease. Immunotherapy is the only available treatment that can modify the natural course of the allergic is, by reducing sensitivity to the immunomodulators such as antigens or allergens. An antigen and an allergen and both cause one's immune system to respond. An allergen is an antigen, but not all antigens are allergens. An antigen is any substance that is capable of causing one's immune system to produce antibodies. They are typically organic, or living, produced proteins. An allergen is any antigen that causes an allergic reaction. A non-allergen antigen could be a bacteria, virus, parasite, or fungus that causes an infection. This could also be something else that causes antibody immune system response, like toxins, chemicals, tissue cells involved in transplants or blood cells from a blood transfusion. An allergen is an environmentally produced substance that causes an allergic reaction, although the substance may not be harmful. Allergens cause no reactions in some individuals, while possibly causing a hypersensitive reaction in others. Common allergens include such things as pollen, plants, smoke, feathers, perfumes, dust mites, toxic mold, food, drugs, animal dander, and insect bites and stings.

The exact mechanisms of how IT works are not fully understood, but they involve shifting a patient's immune response from a predominantly "allergic" T-lymphocyte response to a "non-allergic" T-lymphocyte response.

Current accepted processes for performing allergy immunotherapy include injecting immunomodulators matter in the form of antigen material into patient subjects. This is referred to as subcutaneous immunotherapy (SCIT), requiring a patient to visit a doctor's office for weekly injections. It's is very expensive and time-consuming. A second technique, Sublingual immunotherapy (SLIT), involves the application of allergy extracts (antigens), and allergens placed into a pill form and swallowed by the patient or disposed in "allergy drops" which are placed under the tongue for the allergens/antigens to be absorbed into the oral mucosa. Transdermal patches may have been used without much success and mostly were used for patch testing to see if a patient reacts to various chemicals or allergens.

Of the people who start traditional subcutaneous injected immunotherapy (SCIT), 90% fail to complete their therapy due to needle fatigue and not being able to see a doctor in their office once or more per week for several years. Further, doctors charge for every one of those visits. Further, doctors trained to give injections for allergy are concentrated in high population and upper middle class places. People in rural areas and people who do not live in upper middle class areas cannot get to an allergist for shots. Consider an inner city kid having to ride public transportation and pay a high copay just to get a high risk injection if an alternative therapy were available?!

Allergies are also linked to depression and suicide and are among the top ten reasons for missed work and lost productivity. Lastly, allergies and asthma result in billions of dollars in lost productivity and healthcare costs among the 90% of allergy patients that either never get immunotherapy or fail immunotherapy delivered under its current administration methods.

Immunotherapy basically involves a series of allergy shots given to reduce one's sensitivity to various allergens that may cause an allergic reaction. This immunotherapy can either be venom based or environmentally based. For venom based immunotherapy (VIT), treatments are available for allergies to stings such as honeybees, Yellowjackets, Hornets, paper wasps, fire ants and snakebites. For such things as insect stings, very small amount of the insect venom is injected under the skin in a dilute saline solution. This type of therapy is recommended for all patients who have experienced systemic reaction to insect sting and have specific IgE to venom allergens shown either my skin or blood test. Individuals with a history of a systemic reaction to an insect sting are at an increased risk of subsequent systemic sting reactions. VIT as compared to Environmental Immunotherapy is different than pollins and the such that one might be exposed to in the environment in that VIT is basically associated with allergens that are flown around inside a special injection device that, when counter, may threaten the lives of those who are sent to to it . . . Insect venom allergy or snake venom. The primary offenders associated with VIT are prone primarily insects that sting rather than those that might or, as noted hereinabove, snakes. The insects that sting are typically members of the order of Hymenoptera of the class insect. This can include members of the Vespid family, Yellowjackets, yellow Hornets, white-faced Hornets and wasps. There also the class of Apids, including honeybees and bumblebees. There's also the Formicid family that consists of fire ants and Harvester ants.

To desensitize an individual against a particular venom, the process is to immunize the individual with small and graded doses of the venom. This is compared to the use of an anti-venom which is manufactured via a purified process in another animal such as a sheet. For example, the approved anti-venom for the pit viper (rattlesnake, copperhead and water moccasin) is based on a purified product made in sheet known as CroFab. These anti-venoms are typically administered through intravenous techniques. However, there are some antivenoms for such things as stonefish and redback spider that are administered intramuscularly. These antivenoms are injected after a bite, as they are designed to bind to and neutralize the venom, halting further damage, but do not reverse damage already done. This is compared to desensitizing an individual by small graded doses.

In general, and antigen is any structural substance that serves as a target for the receptors of an adaptive immune response or, alternatively, and more simply stated, and antigen is any substance that causes an immune system to produce antibodies against it. An allergen is a type of antigen that produces an abnormally vigorous immune response in which the immune system fights off a perceived threat that would otherwise be harmless to the body. These reactions are termed allergies. Thus, by providing small graded doses of venom as the allergen, this would produce some type of immune response in the immune system that would generate anti-bodies to fight off the perceived threat. For small doses, the immune system can initially accommodate this and, as a doses increase, the immune system will continue to adapt and build up antibodies to this allergen, i.e., the venom of the particular insect or snake or other such. These allergens associated with the venom immunotherapy are specifically associated with allergens that originate from the internal organs of animals, insects or reptiles.

Currently, most allergens associated with venom immunotherapy are not readily reimbursed when received from a pharmacist for the simple reason that the NDC code is not included in the database to which the pharmacist has access. Without an NDC code in the database, the pharmacist cannot access that information. By not being able to access information, the pharmacist cannot interface with a benefits provider for reimbursements nor can they have access to the Average Wholesale Price (AWP), which is the benchmark that has been used for many years for pricing and reimbursement of prescription drugs for both government and private payers. Initially, this AWP was intended to represent the average price that wholesalers used to sell medications to providers, such as physicians, pharmacies, and other customers. However, the AWP is not a true representation of actual market prices for either generic or brand drug products. AWP has often been compared to the "list price" or "sticker price", meaning it is an elevated drug price that is rarely what is actually paid. AWP is not a government-regulated figure, does not include buyer volume discounts or rebates often involved in prescription drug sales, and is subject to fraudulent manipulation by manufacturers or even wholesalers. As such, the AWP, while used throughout the industry, is a controversial pricing benchmark.

The AWP may be determined by several different methods. The drug manufacturer may report the AWP to the individual publisher of drug pricing data, such as Medi-Span. The AWP may also be calculated by the publisher based upon a mark-up specified by the manufacturer that is applied to the wholesale acquisition cost (WAC) or direct price (DIRP). The WAC is the manufacturer's list price of the drug when sold to the wholesaler, while the DIRP is the manufacturer's list price when sold to non-wholesalers. Typically a 20% mark-up is applied to the manufacturer-supplied WAC or DIRP, which results in the AWP figure.

The publishers then in turn sell these published AWPs to government, private insurance, and other buyers of prescription drugs, who use these data tables to determine reimbursement and retail prices. Because AWP is a component of the formulas used to determine reimbursement, elevated AWP numbers can drastically increase the dollar amount that government, private insurance programs, and consumers with coinsurance must pay.

Pharmacies typically buy drugs from a wholesaler and then sell them to the public. Many patients have coinsurance or copayments, where they only pay for a portion of their prescription cost. The insurance company then pays the rest of the cost (the reimbursement) to the pharmacy. Insurance companies include prescription benefit manager (PBM), health maintenance organization (HMO) or government programs, such as Medicaid or Medicare Part B or D. In addition, the pharmacy receives a dispensing fee for filling the prescription. Fees are, for example, set between $3 to $5 per prescription, but may vary by state.

Reimbursements are based on AWPs. However, pharmacies purchase drugs based on the WAC. The difference between the WAC (what the pharmacy actually paid for the drug) and the reimbursement from insurance (based on AWP) is known as the spread, and equates to the profit that the pharmacy receives.

Market pricing on brand drugs tend to be about 16.6 percent less than the AWP. However, the relation of AWP to generic pricing is not clear. Older generics tend to have a large spread between the AWP and WAC, which in turn gives a large spread, and higher profit margins for the pharmacy or other provider of the drug. Many payers, such as PBMS or HMOs, will determine a maximum allowable cost (MAC) pricing on generics to avoid being overcharged. Newer generic products, compared to older generics, may not have as favorable of a spread, thus the need for MAC.

Collusion between AWP publishers and wholesalers to artificially inflate the AWP, and in turn increase the spread, has led to court cases in the U.S. In these cases, it was alleged that increasing the spread benefited the wholesaler because customers (pharmacies and large institutions) were more likely to buy from them than a competing wholesaler where the spread was not as desirable. The publisher of AWPs profited because pharmacies were more likely to buy the pricing lists from the publisher that noted the higher AWPs used in calculating the spread, than to buy them from other publishers with lower AWPs. Due to this pricing fraud, many payers, including government payers, are no longer using AWP for pricing, and are switching to other more transparent pricing benchmarks, such as WAC or AMP (average manufacturers price). However, AWP may still be found in use in the U.S. because it has been the standard for decades.

However, in order for a pharmacist to access the AWP and to be able to interface with benefits providers, the product associated with an NDC must be in the database. Currently, nonvenoms are an item that does not exist in the database.

SUMMARY

A method for creating a consolidated compound for delivering an immunomodulatory and imiquimod to a patient is provided. The method comprises the steps of providing a plurality of containers of concentrated immunomodulator extract, for each container of concentrated immunomodulator extract, diluting the immunomodulator extract with a predetermined dilutant in an associated sterile container approved for such dilution and to a desired dilution by transferring a desired quantity of the concentrated immunomodulator to the associated sterile container, the associated sterile container having a defined volume of diluted immunomodulator after dilution thereof, such that there is an associated sterile container for each container of concentrated immunomodulator extract, providing a viscous encapsulation material that is able to carry immunomodulators across the dermis of a patient and having a defined volume disposed within a container, the defined volume divided into a plurality of dispensable increments, selecting a prescribed amount from each of the sterile containers associated with each of the containers of concentrated immunomodulator, the prescribed amount for each of the sterile containers defined as that amount of the diluted immunomodulator extract required to provide a number of doses equal to the number of dispensable increments from the container containing the viscous encapsulation material, a dose providing a desired therapeutic effect to a patient for each of the diluted immunomodulator extracts, introducing the selected amount of each of the diluted immunomodulator extract into the viscous encapsulation material, introducing an amount of imiquimod into the viscous encapsulation material, and mixing the introduced amount of each of the diluted immunomodulator extracts and the introduced amount of imiquimod with the viscous encapsulating material in which it was introduced.

BRIEF DESCRIPTION OF THE DRAWINGS

For a more complete understanding, reference is now made to the following description taken in conjunction with the accompanying Dr

DETAILED DESCRIPTION

Figure 1:
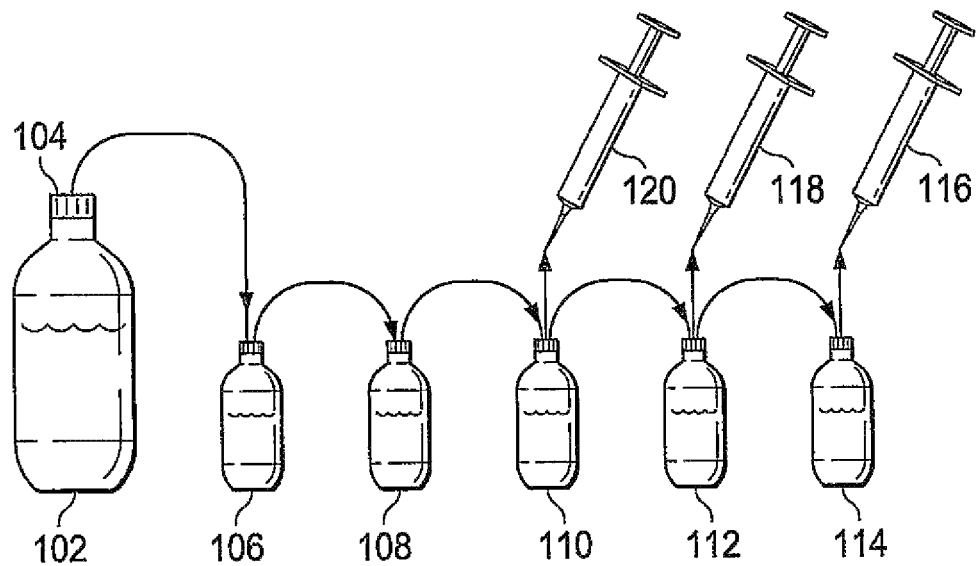

Referring now to the drawings, wherein like reference numbers are used herein to designate like elements throughout, the various views and embodiments of an individually customized allergy cream for individual patient profile are illustrated and described, and other possible embodiments are described. The figures are not necessarily drawn to scale, and in some instances the drawings have been exaggerated and/or simplified in places for illustrative purposes only. One of ordinary skill in the art will appreciate the many possible applications and variations based on the following examples of possible embodiments.

The principles of the present disclosed embodiment include a process that involves the use of transdermal carrier creams infused with antigens that can be applied to the patient's skin surface. Further, the antigens can also be carried across the dermal layer along with antihistamines, anti-inflammatory medications, imiquimod, and steroids as well as other drugs that may prevent a severe allergic reaction in patients and thus possibly avoid life-threatening anaphylactic reactions. The antigens can also be carried to various depths based upon the physician's requirements. Some transdermal carrier creams penetrate just beyond the deepest skin layer where many of the human cells that recognize antigens as foreign invaders reside. If the physician wishes to treat the patient in a more traditional manner, some transdermal carrier creams can penetrate the patient well below the skin and reach areas of high vascularity thus pushing the antigens into the blood stream much the same as utilizing a hypodermic needle.

The transdermal carrier creams can be used to carry only antigens into the body or they can be used in conjunction with antigens and other medications that can be carried across the skin as combination therapies for allergies.

Referring now to FIG. 1, there is illustrated a depiction of a technique for diluting immunomodulators such as antigens, as one example. Preparation of a diluted antigen is performed first by receiving a bottle of extract concentrates from an approved vendor. These are formulated in a given weight/volume (w/v) format with a given antigen associated therewith. For typical antigens such as those associated with the cat antigen, these are relatively well controlled. Typically, a vendor will provide an extract for a single antigen or allergen. Allergens such as pollen and the such are not as well controlled due to the technique for collecting such. In any event, there are typically very few approved vendors for these extracts and allergist typically receives these vendor provided concentrates in a sufficient quantity to make the necessary diluted solution.

Allergen extract is typically comprised of a non-allergenic material, a non-allergenic protein and an allergenic protein. The extraction solutions can be aqueous containing saline and phenol work could be a glycerinated solution. The allergen is added, the units of measure are sometimes referred to as "AU" for "allergy units," typically used for mites. These are referred to as "AU/mL." For such things as grass and cat, the term "BAU" is used for "bioequivalent units." For other allergens, the terminology is, for example, 1:20 w/v, which stands for 1 g source material per 20 mL of fluid. The relationship between BAU and 1:20 w/v depends upon the extract. In any event, there is a defined amount of extract contained within the concentrate.

When concentrated extracts are formulated by an authorized vendor, they are typically provided in standardized versions and non-standardized versions. In standardized versions, they typically are provided in a 50% glycerin dilutant. They can either be a single allergen extract or they can be a mix. For example, one can obtain a "9 Southern Grass Mix (concentrate)" which contains equal parts of: 2 Bermuda at 10,000 BAU/mL, P27 7 Grass at 100,000 BAU/mL, 15 Johnson at 1:20 w/v. For non-standardized extracts, these are typically provided in either a glycerin dilutant or an aqueous dilutant such as saline. They can be a single extract or a mix. Thus, whenever a concentrated extract is referred to hereinbelow, this refers to a formulation that is provided by an authorized vendor that can be diluted in accordance with the processes described hereinbelow. These are typically provided in the 50 mL bottles with a needle compatible.

Referring back to FIG. 1, the extract concentrate is disposed in a bottle 102. This is a sterile concentrate that has an injection stoppered top 104. There are provided a plurality of five 5 mL sterile injection stoppered bottles 106, 108, 110, 112 and 114, although there could be more and the bottles or containers could be larger than 5 mL. Each of these bottles has disposed therein a defined amount of dilutant, depending upon what the final required to be. Typically, the amount of dilutant is 4.5 mL. The procedure is to, first, extract a defined amount of the concentrated extract from the bottle 102 and dispose it in the bottle 106. This is facilitated by the sterile hypodermic that is inserted through the stopper at the top of the bottle 102 to extract concentrate and then the hypodermic is inserted to the stopper in the bottle 106 to inject extract from bottle 102 into bottle 106. Typically, the concentration in the concentrated extract bottle 102 is 1:20 w/v. This will result in a dilution of 1:10 in bottle 106. If the amount injected is 0.45 mL. Then, 0.45 mL of the diluted solution from bottle 106 is then extracted and inserted into bottle 108, resulting in a 1:100 dilution of the original concentrate in model 108. The process is repeated up to the bottle 114 to provide a solution that is at a dilution of 1:100,000 of the original concentrate. This is a conventional way to provide a selected dilution of the original antigen. However, it should be understood that any concentration level can be provided from one bottle to the next. Purpose of using the sequential bottles is to allow an achievable portion of one bottle to be distributed to the next bottle, rather than trying to extract a very small amount of the initial concentrated extract. Typically, an allergist will then extract from the desired dilution an amount of the diluted antigen for injection percutaneously. Typically, desensitization is achieved by using the most diluted antigen level initially and sequentially moving up to a higher concentration level over time 1.

Illustrated in FIG. 1 are three hypodermic needles, one selecting a "dose" from bottle 114, and labeled hypodermic 116, a second hypodermic needle 118 for retrieving a dose from bottle 112, a third hypodermic needle 120 for extracting a dose from bottle 110. Each of the hypodermic needles 116, 118 and 120 will contain a different diluted dose. These would typically be separate needles in the event that the allergist or medical professional is injecting a patient. For other purposes, they could be the same needle, depending upon the dose or concentration required. A "dose" is defined the amount all the diluted product that would be required for the desired immunotherapy. This is defined by the medical professional. If, for example, bottle 112 were utilized, it may be that 1 mL of diluted solution constituted a "dose." It could be that less than 1 mL constituted an "dose."

Figure 2:
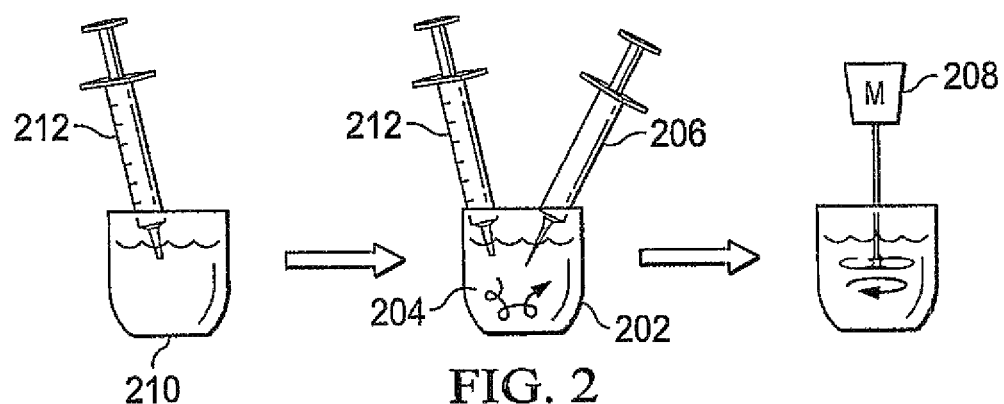
Figure 3:
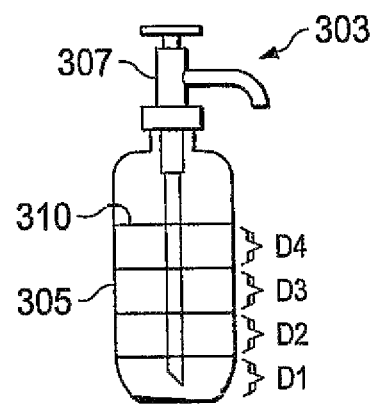
Figure 4:
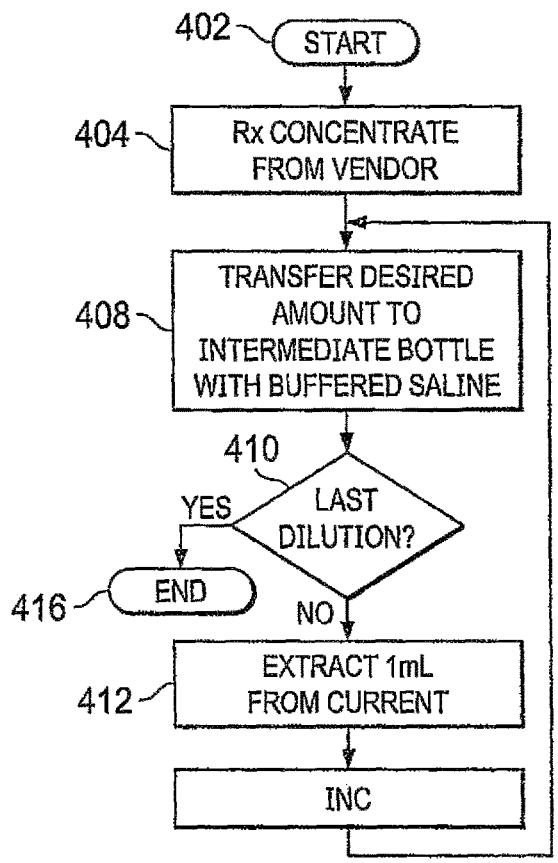
Figure 5:
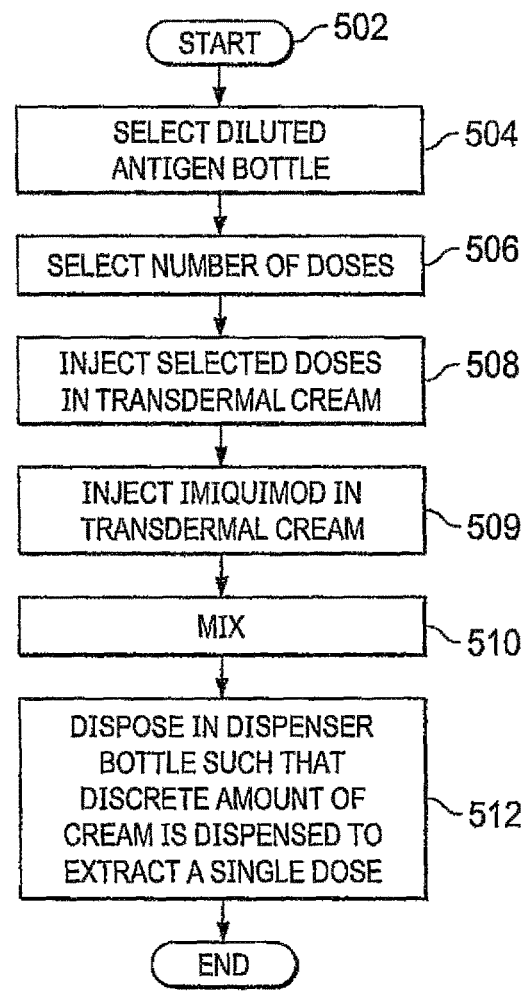
Figure 6:
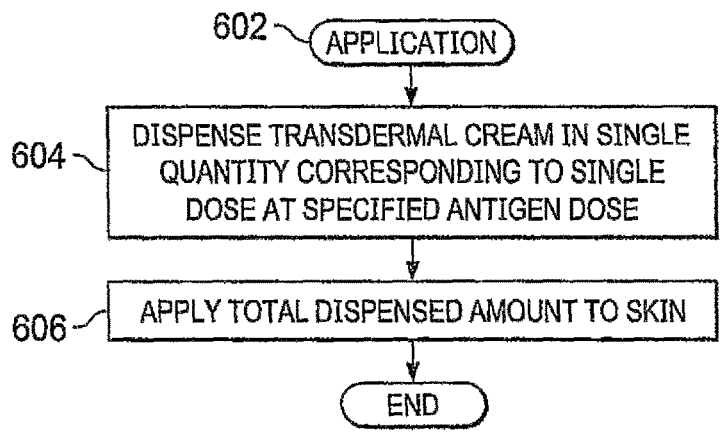
Figure 9:
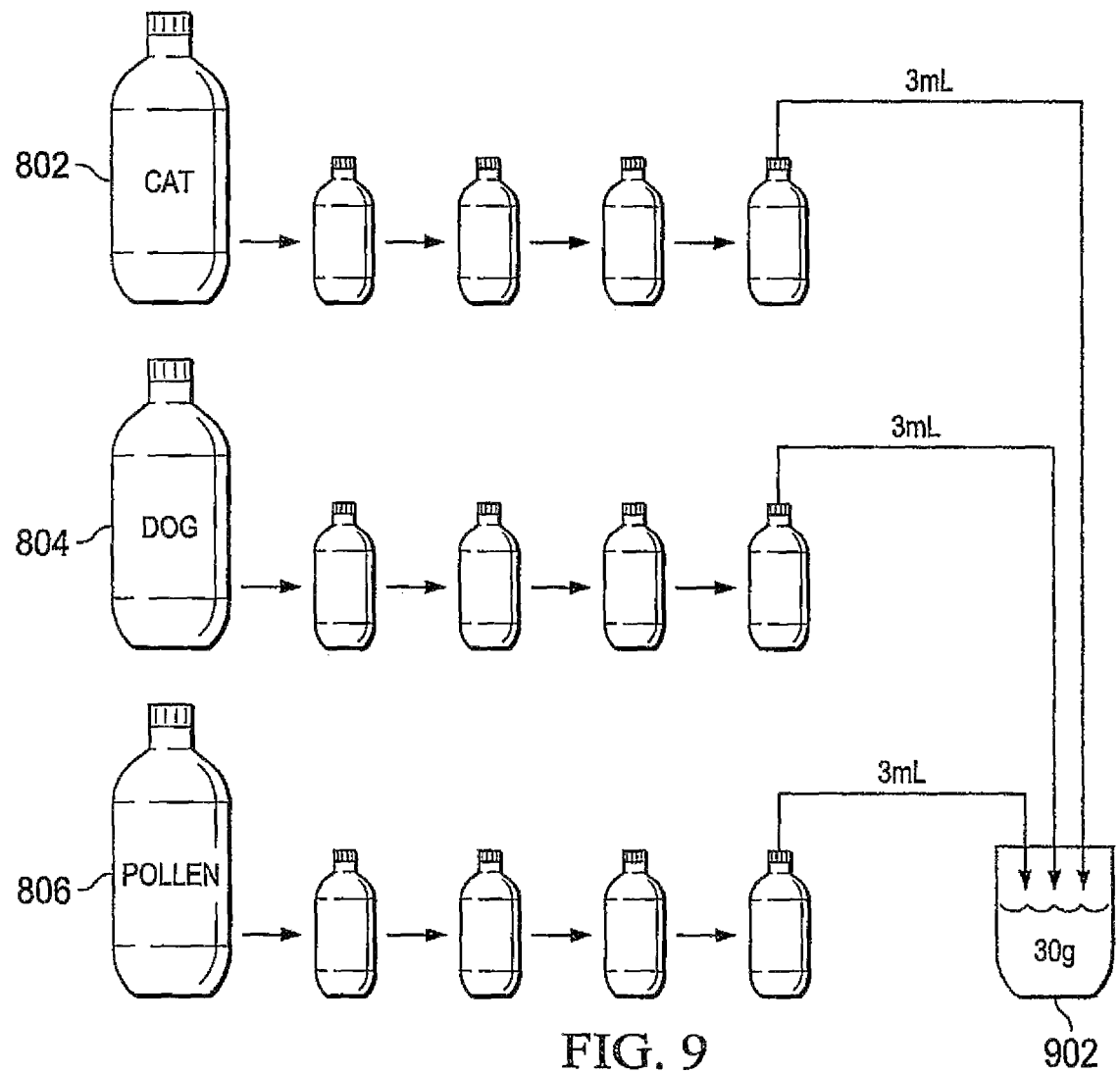
Figure 10:
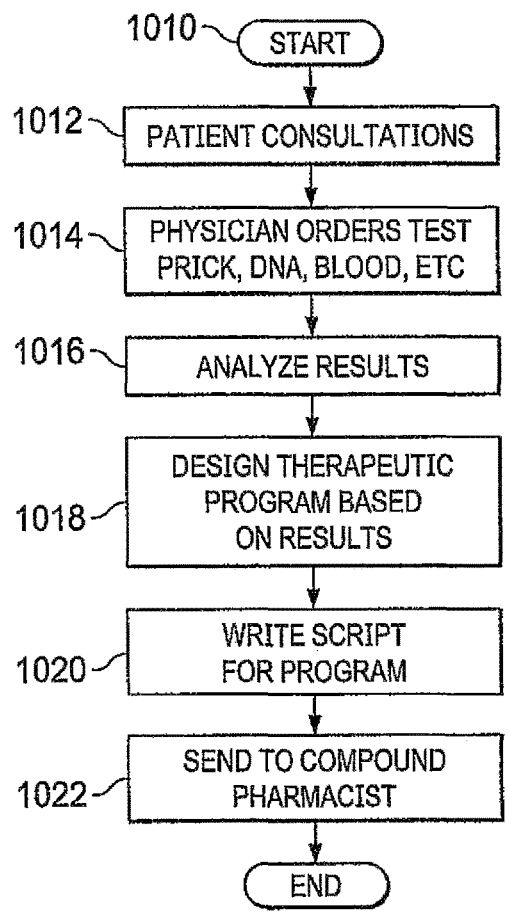
Figure 11:
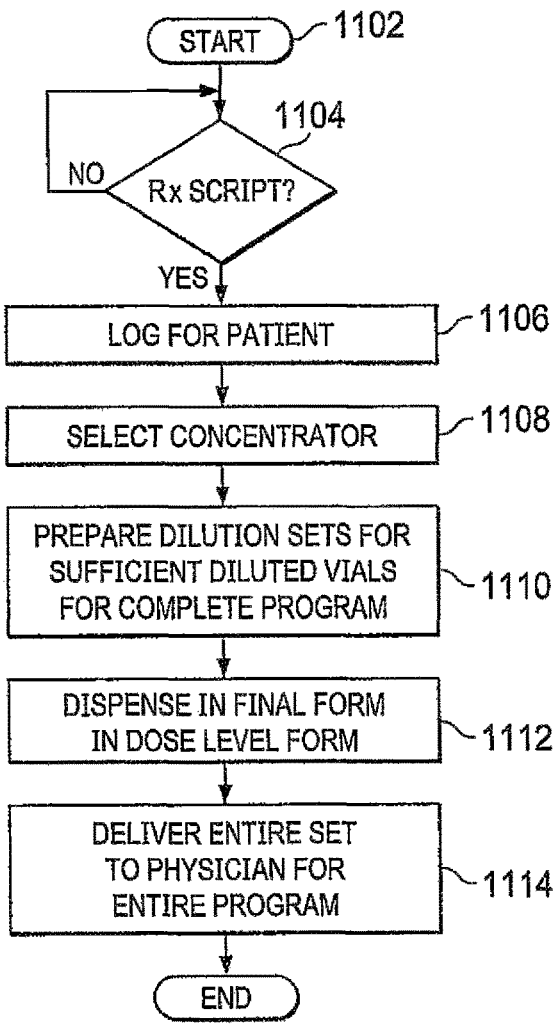

Referring now to FIG. 2, there is illustrated a diagrammatic view of injecting a dose into a container 202 which contains a quantity of transdermal cream 204, which transdermal cream is a viscous encapsulation material for containing this dose in an emulsion. The transdermal cream may also have injected and mixed therein a quantity of imiquimod. Imiquimod is a medication, usually given within a cream at a particular concentration (often 5% by weight, but formulations may vary between 0.5% to 9%) that acts as an immune response modifier, which serves to increase the activity of the body's immune system. U.S. Pat. Nos. 5,238,944 and 5,736,553 to Wick et al., which are herein incorporated by reference in their entirety, describe certain imiquimod compositions. One such cream composition is as follows:

TABLE 1

| | % by Weight |
|---|---|
| Oil Phase | |
| 1-Isobutyl-1H-imidazo[4,5-c]-quinolin-4-amine | 5.0 |
| Isostearic acid | 25.0 |
| Benzyl alcohol | 2.0 |
| Cetyl alcohol | 2.2 |
| Stearyl alcohol | 3.1 |
| Petrolatum | 3.0 |
| Polysorbate 60 | 3.4 |
| Sorbitan monostearate | 0.6 |
| Stearic acid | — |

TABLE 1-continued

| | % by Weight |
|---|---|
| Aqueous Phase | |
| Glycerin | 2.0 |
| Methylparaben | 0.2 |
| Propylparaben | 0.02 |
| Purified water | 53.48 |

It will be understood, however, that other formulations, such as other formulations disclosed in U.S. Pat. Nos. 5,238,944 and 5,736,553 to Wick et al., may be used.

Imiquimod signals to the innate arm of the immune system through the toll-like receptor 7 (TLR7), which is commonly involved in pathogen recognition. Cells activated by imiquimod secrete cytokines. There is also evidence that application of imiquimod to the skin can lead to the activation of Langerhans cells, which migrate to the local lymph nodes to activate the adaptive immune system. Other cell types activated by imiquimod include natural killer cells (a type of cytotoxic lymphocyte), macrophages, and B-lymphocytes. All of this combined contributes to the strong antitumoral activity of the compound. Imiquimod has historically been used to assist in the treatment of skin conditions such as warts, genital warts, superficial basal cell carcinoma, and actinic keratosis. A particular formulation of imiquimod is $C_{14}H_{16}N_4$, but other formulations exist and may be used.

A container 210 containing imiquimod may be provided. A dropper 212 may be used to collect the imiquimod from the container 210. It will be understood that the dropper 212 is only illustrative of one way to collect the imiquimod from the container 210 and any other way of collecting and measuring the amount collected may be used. The amount collected may be the amount needed for a single dose of imiquimod appropriate for the patient. A typical dose of imiquimod may be 250 mg when already in a cream, or an amount that can be applied to 25 square centimeters of skin. The amount of imiquimod collected may also be an amount for providing the desired amount imiquimod proportional to the amount of transdermal cream needed. For example, an amount of imiquimod that will comprise 5% by weight of the transdermal cream 204 may be collected. The dropper 212 is then used to inject the imiquimod into the container 202 and into the transdermal cream 204.

A hypodermic needle 206 is also illustrated which contains a single dose or multiple doses of diluted antigen as noted hereinabove, the last bottle 114 will have 5 mL of diluted antigen disposed therein. If the allergist determines that a dose is 1 mL, then a single dose could be disposed in the quantity of transdermal cream 204. If the allergist or medical professional determined that the container 202 should contain three doses, 3 mL would be selected and disposed within the container 202. It is noted that one limitation of the bottle 114 for the 1:100,000 dilution level or the bottle 112 for the 1:10,000 dilution level each has a finite volume. Since the finite volume is, in this example, 5 mL, and if the dose is determined to be 1 mL, then only 5 doses could be provided for a getting a given dilution process. Thus, only a maximum of five doses could be disposed within the container 202. Once the imiquimod and the diluted solution of the immunomodulators in the form of an antigen is injected into the transdermal cream 204, it is subjected to a mixing operation via a mixer 208. In other embodiments, the imiquimod may be injected into the transdermal cream 204 and mixed before the diluted antigen is mixed into the transdermal cream 204, or vice versa.

A transdermal cream is basically a viscous encapsulation material that includes a base that is provided to transport drugs through the skin. There are some types of transdermal bases or creams that allow for delivery of up to four drugs or compounds through the skin simultaneously. The creams are different than transdermal patches in that they are rubbed on a particular area of the skin and are absorbed through the skin in a very short period of time and are well suited to small molecule antigens. One such transdermal cream is that manufactured by PCCA under the trademark Lipoderm®. This base is utilized for the percutaneous absorption of drugs through the skin. As such, not only can antigens be provided in a particular dose within the transdermal cream, but other drugs such as antihistamines, imiquimod, and pain medications can also be provided, depending upon the particular needs of a patient. The desire for the immunomodulators in the form of antigens is that they be disposed within the subcutaneous region just beneath skin or the stratum corneum, which is the outermost layer of the epidermis. This layer, of course, very thin thickness throughout the body. The desire is to allow, via the transdermal cream, the transport of the immunomodulators through this stratum corneum to the subcutaneous tissue or the hypodermis.

Referring now to FIG. 3, there is illustrated a diagrammatic drawing of a distribution pump 303 that has a container 305 and a pump head 307 associated therewith. Disposed within the interior of the container 305 is a quantity of transdermal cream that represents four doses of the antigen at the desired dilutant level and imiquimod. Thus, for example, the last bottle 114, as depicted in FIG. 1, would have around 5 mL of diluted antigen disposed therein. If the desired dosage for the patient was 1 mL, then 4 mL would be extracted from the bottle 114 to provide 4 doses and disposed within a sufficient amount of transdermal cream to rise to a level 310 within the container 305. The dosage increment is that represented by at least one full pump stroke or a defined number of pump strokes. For example, the directions might state that a single full pump stroke represented a single dose and that was what was to be applied at a particular time in accordance with the directions of a medical professional. It might be that multiple strokes are required per dose. In that case, the directions would indicate that the dose is to be applied would require that number of pump strokes. All that would be required would be to know the amount of transdermal cream that was required to fill the container 305 to the level 310 and then inject for dosages therein and mix the material. The transdermal cream could be a transdermal cream that already had a predetermined amount of other medications contained therein such as antihistamines, imiquimod, and/or pain medication.

In addition, a sealed straw type tube could be used instead of the metered pump. In this type of delivery device, a premeasured amount of the viscous material, i.e., the transdermal cream, can be provided that could represent, for example, a single dose. However, as described hereinbelow, the amount of cream for this single dose represents a volume of cream that contains, in one example, a single diluted dose of a single concentrated extract or, alternatively, a single dose each of multiple concentrated extracts. For the latter, all that is required is that the volume of the transdermal cream first be defined and then the single dose of each of the concentrated extracts disposed therein.

The transdermal cream or carrier is, as described above, a viscous encapsulation material for encapsulating a finite amount of immunomodulators or antigen therein. This transdermal cream is basically a consolidator. As such, more than a single immunomodulator can be disposed within the cream of. This, of course, depends upon what the smallest increment of dosage is comprised of. If, for example, the container 202 in FIG. 2 contained 30 g of encapsulation material and it was possible to extract a single gram per application, this would mean that 30 doses of the immunomodulator would have to be injected or disposed within the encapsulation material, i.e., the transdermal cream. To facilitate this, the dilution must be at the appropriate level. If, for example, 3 mL of diluted immunomodulator were added to the 30 g of viscous encapsulation material, then 0.3 mL of the diluted immunomodulator would constitute a single dose. In that example, suppose that the allergist or medical professional determined that this was the case and required five separate immunomodulators to be disposed within the viscous encapsulation material. This would then require the consolidator to basically add 3 mL of diluted immunomodulators from the desired vial or bottle having the desired dilution of the desired immunomodulators or antigen. For this example, this would require three injections, each being 3 mL. The actual increase in the volume of the viscous encapsulation material disposed within the container, containing 30 g of viscous encapsulation material would only be slightly greater than that value. If the distribution mechanism were able to distribute a single grand of viscous encapsulation material as a single "dose" of the material, this would actually provide a single dose of five different antigens in a single application of 1 g of the material onto the skin. In the example of FIG. 3, this would require, for each volume of eight dose of viscous encapsulation material, that the appropriate amount of immunomodulators or antigen be disposed therein.

Referring now to FIG. 4, there is illustrated a process flow for the embodiment of FIG. 1. This is initiated at a process block 402 and then proceeds to block 404 wherein a certain amount of concentrated extract is received from a vendor, this being a qualified or authorized vendor for the extract. This is typically at a predetermined concentrate level of, for example, 1:20 m/v. The process then flows to a block 408 wherein a defined quantity of, for example, 0.45 mL is transferred to a 5 mL bottle which already has a quantity of 4.5 mL buffered saline solution disposed therein. The process then flows to a block 410 to determine if this was the last dilution step needed, as described hereinabove, depending upon what level of dilution is necessary. If, for example, by steps of dilution are required for a particular patient, and all five steps would be processed. However, it is not necessary to do all five steps if an intermediate dilution is required. This essentially customizes the overall operation for a particular patient. Further, the industry is so regulated such that only 5 mL bottles can be utilized for this dilution process. Thus, it will only be a maximum of 5 mL of diluted material available at any step prior to proceeding to the next step. Thus, if all 5 mL are required, then the next step is not desired or useful. If it is not the last dilution step, the process flows to a block 412 to extract 0.45 mL of diluted antigen from the current 5 mL bottle and then flows back to the input of the process block 408 after incrementing the bottle count. This continues until the last dilution, at which time the process flows from the block 410 to a terminate block 416.

Referring now to FIG. 5, there is illustrated a process flow for combining the selected diluted antigen with the viscous encapsulation material or transdermal cream, which is initiated at a block 502 and proceeds to a process block 504 to select the diluted antigen bottle or bottles from which to extract the dose or doses. At a process block 506, the prescribed number of doses is extracted from that particular bottle, keeping in mind that only a maximum of 5 mL of the diluted antigen is available. At the process block 508, the selected number of doses of the diluted antigen is injected into a predetermined quantity of transdermal cream from one bottle for a single antigen mixture and from multiple bottles for a multiple antigen mixture. At step 509, imiquimod is injected into the transdermal cream at a desired amount. The transdermal cream may also already contain other medications, such as imiquimod, or those other medications may be mixed into the transdermal cream at a later time. The process then flows to block 510 to mix the injected cream. The process then flows to a block 512 to dispose the mixed transdermal cream in a dispenser bottle such that a discreet amount of transdermal cream can be dispensed so as to extract a single dose of the diluted antigen contained therein.

Referring now to FIG. 6, there is illustrated a process flow for the application of the transdermal cream. This is initiated at a process block 602 and then the flow proceeds to process block 604. The transdermal cream is dispensed in a single quantity that corresponds to a single dose at the specified antigen dose. This instruction is provided by a medical professional and, if followed, is substantially identical to the subcutaneous injection of the same dose directly from the hypodermic needle. Once dispensed, this amount of transdermal cream is applied to the skin by the patient or a medical professional, as indicated by a process block 606.

As an example, suppose that the container provided to the patient contained in 30 g of viscous encapsulation material or transdermal cream. In this material was contained a plurality of doses such that a single dose is contained within 1 g of material. The physician might provide a schedule or regimen that, in the first week requires one dose to be applied on Monday, Wednesday and Friday of that week. This would require the patient to dispense a single gram of material on each of those days constituting a single dose for each of those days and apply it. In the next week, the regimen is to apply two doses three times a week on Monday, Wednesday and Friday, requiring the patient to dispense 2 g of material for each of those dates. In the third week, the regimen might require three doses to be applied three times in that week on Monday, Wednesday and Friday. This requires the patient to dispense 3 g of material for each of those days and apply it. In the fourth week, the regimen might require the patient to dispose four doses of the material onto the skin on three days of the week, Monday, Wednesday and Friday. This would require the patient to dispense 4 g of material for each of those three days and apply it.

The application transdermal cream could be to any portion of the skin, but preferably, it would be to an area that represents an area of some type of allergic reaction. If for example, the patient experiences some type of rash on their neck, they would apply the mixture to that area of the body. If not, it could be applied only to the arm.

Referring now to FIG. 7, there is illustrated in overall flow of the operation of moving concentrated antigen from a vendor to an end user. As noted hereinabove, the liquid antigen in a concentrated extract was first received from a vendor, which is basically a combination of a single antigen or antigens suspended in a sterile agent. This is indicated by a block 702. The antigen is then diluted from this extract to a desired diluted level, as indicated by a process block 704. This is combined in a block 706 with a sterile viscous encapsulation and containment material, i.e., a transdermal cream, for distribution. This, as described hereinabove, will typically be a defined number of doses of a single diluted antigen or multiple diluted antigens, wherein a dose is again defined as being a typical dose that a medical professional would administer to a patient in an office visit necessary to achieve a therapeutic result. This is either transferred as a combined antigen (diluted)/encapsulation product for storage on a shelf, as indicated by a block 712, or it would be transferred to a medical professional for management and disposition.

Referring now to FIG. 8, there is illustrated a diagrammatic view of three different extracts of antigens/allergens 802, 804 and 806. Each of these is for a particular antigen or allergen. The first two are for antigens respectively associated with a cat and a dog. The third is for an allergen associated with pollen. They are each diluted in accordance with the process described hereinabove with respect to FIG. 1. As illustrated, the antigen extract in bottle 802 is transferred as a diluted level to either an encapsulation material in a container 810 or 812, each at a different diluted level. This is similarly the case with respect to the antigen in bottle 804 and the allergen in 806 wherein the diluted level of the antigen in the bottle 804 is disposed in containers 814 and 816 and the diluted level of the allergen in bottle 806 is disposed in containers 818 and 820. Typically, any extract will be 100% pure with respect to the particular extract. These concentrated extracts are not typically mixed, which is typically a function that the medical professional will perform. This, of course, is a customized mixture for a particular patient. For storage on the shelf, the operation of FIG. 8 will be facilitated in order to ensure that the containers 810-820 contained only a single antigen. Thus, when transferring the container to a store, for example, this would be stored on the shelf as a single allergen combination. This is for a situation where in a single bottle or container of the viscous encapsulation material or transdermal cream would be associated with only a single immunomodulator or antigen.

Referring now to FIG. 9, there is illustrated an alternate disclosure to that of the embodiment of FIG. 8. In this embodiment, each of the immunomodulators or antigens at the concentrated levels in the bottles 802-806 are diluted in accordance with the process noted hereinabove wherein they are sequentially diluted in the associated 5 mL bottles. However, note that only a maximum of 5 mL can be extracted from a given bottle at the last dilution level. If, in this example, it is desired to distribute a predefined number of doses to a final carrier 902 having 30 g of viscous encapsulation material or transdermal cream and imiquimod disposed therein and each dose will be associated with a single gram of that material, then the amount of diluted antigen must be adjusted such that single dose is contained within 0.3 mL of the material. Thereafter, if 3 mL of antigen is extracted from a given bottle, this constitutes 30 doses such that a single dose will be associated with a single gram of the final encapsulation material. In this example, from each of the last dilution bottles for each of the concentrate bottles 802-804, 3 mL in extracted and inserted within the container 902 containing 30 g of material. Thus, for each gram of material, there will be a single dose of the particular antigen associated there with. Thus, encapsulation material in the container 902 now acts as a consolidator of all of the antigens. It is noted that, if the starting material is, for example, 30 g, and there is provided a dispenser capable of dispensing a single gram of material at a time, the addition of the antigens might increase the volume slightly. This, of course, depends upon what the volume of cream constitutes for a gram of cream for the viscous encapsulation material. This may increase the overall quantity or volume by a small percentage, but, in general, the overall volume is not increased. If, for example, a large number of antigens were introduced into the viscous material 902 in this matter, the initial volume of the viscous material magnitude could be decreased to account for such, yielding a total container having 30 g disposed therein which is comprised of the viscous encapsulation material and all of the particular antigens or immunomodulators desired.

As a distribution mechanism, all that is necessary is for the consolidator to have available a kit with the appropriate dilution bottles and the concentrated extract for each concentrated extract desired. The amount of material from one bottle to the next is then defined such that the consolidator can accurately control the amount of diluted antigen that is in the last bottle. This would then allow the consolidator to create the container 902 containing the appropriate amount of doses of antigens therein. Since a particular kit may have a single bottle of concentrated extract therein, there may be multiple dilution bottles provided to allow more than one final dilution to provide another consolidated mixture of transdermal cream with a different combination of antigens.

Allergies are the leading cause of asthma and asthma is a debilitating, life threatening, disease. It costs millions of dollars to treat. Allergy immunotherapy is the only known treatment for the prevention of asthma and further is the only treatment that may possibly reverse the disease. The topical antigen allergy treatments will likely affect 90% of allergy and asthma patients.

Referring now to FIG. 10, there is illustrated a flowchart depicting the overall operation of a physician providing a therapeutic program to a patient. In this operation, a physician is able to evaluate the allergen needs of a particular patient and prescribe a particular program for that patient and effectively implement such program. The operation in FIG. 10 is initiated at a block 1010 and proceeds to a function block 1012, wherein a patient enters into a consultation with a physician for the purpose of determining sensitivities to certain allergens. In a block 1014, the physician orders various tests to determine sensitivities of a particular patient to one of multiple allergens. This can be facilitated through a prick test, through a DNA test, through a blood test, or any other technique for determining sensitivities to particular allergens. The physician typically runs the tests at their office and can determine from, for example, a prick test, the sensitivities on a relatively expedient basis. In some embodiments, the test may be analyzed by the physician, as indicated by a block 1016. Of course, the particular lab that provides the results may also provide an analysis therewith. Similarly, the entire testing process can be out-sourced to another lab or testing facility.

After the results have been analyzed, the program proceeds to a block 1018 wherein the physician designs a therapeutic program based on the results. This therapeutic program determines the particular allergens to which a patient is sensitive, which determined allergens will define what allergens must be used for desensitization. The program typically involves first introducing subcutaneously a small dosage of the actual allergen or allergens to which the patient is sensitive. This can be done on an allergen-by-allergen basis or, preferably, multiple allergens can be introduced at the same time. Typically, the first dose is a small dose that is introduced multiple times over the course of a predefined period of time. At the end of this first time, a second and higher dose of the allergen or allergens is introduced over a second time period at defined increments of introduction. Each introduction of the allergen is defined as a "dose." This overall process continues until a sixth dose level is provided, this being the maintenance dose. This particular maintenance dose is the highest dose that an individual is expected to tolerate. Any higher of a dose may not be beneficial overall and may provide some harmful effects to the patient.

Once the program has been designed for a particular patient, i.e., the particular allergens that are necessary for the defined program and the particular dosages, a script is then written for the program to be delivered to a compound pharmacist. This is indicated at a block 1020. This is then sent to the compound pharmacist, as indicated by block 1022. In general, the physician is trained to understand for a particular patient, i.e., by sex, age, weight, etc. or just general medical condition, a particular starting dose for particular allergens or combinations thereof. The physician will be provided with charts and the such to determine what allergens can be combined in a single introduction dose as a single allergen or as a combination with other allergens. Once the initial dose is defined, standard operating procedure defines the increasing doses therefrom. Thus, once the physician defines the initial dose, it can then be assured that all the remaining dosages at the higher concentration levels will be consistent. Further, once the program is designed, it is designed such that all of the allergens are extracted from the same batch. If, alternatively, the physician were to order the first set of doses at the first concentration level for the first period of time at a different time than the last concentration level for the last maintenance dose, it is possible that they would be extracted from a different batch which would have different concentrations and the such. If it is all derived from the same initial batch, the desensitization from one concentration level to another can be fairly well guaranteed and provide the physician with a relatively high degree of confidence in the escalating concentrations between doses in different periods of time.

Referring now to FIG. 11, there is illustrated a flowchart depicting the operation at the compound pharmacist. The program is initiated at a block 1102 and then proceeds to a decision block 1104 to determine if a script has been received for a particular patient from a physician. This script will indicate to the compound pharmacist the overall program for allergen desensitization. The program flows to a block 1106 to create a log for that patient and into a function block 1108 to select the various concentrations as the basic concentration for each allergen or allergens that is specified by the script. It may be that, for example, a physician has determined that the patient is allergic to dog, cat and hay. The compound pharmacist would then select a file for each of these allergens which would be at a base concentration level, as described hereinabove with respect to FIG. 1. The pharmacist then prepares the various dilution sets from the highest concentration maintenance dosage to the lowest concentration starter dose to provide sufficient diluted packaged doses of the respective doses for the complete program. It is important that all doses for the entire program from the lowest dose to the highest dosage be provided from the batches. There will be more than enough initial base concentration to provide the final diluted set of packaged doses. These base concentration vials can be reused multiple times by the pharmacist. This is indicated by block 1110. This is then dispensed in a final form, as indicated by block 1112 in a final form at various dose levels. It may be that the packaging requires each concentration level to have a finite number of doses associated therewith and these doses can be provided in a single packaged dose or they can be provided in separate packaged doses, each associated with a single dose at that associated concentration level. Each of these packaged doses is sterile. That is, when they leave the compound pharmacist, they will have a seal disposed thereover which, upon breaking the seal, results in an unsterile environment. If each dose is a single packaged dose, the physician can be assured that the physician or technician, when administering this dose, starts with a sterile dose.

This final form of dosages will be then delivered to the physician in an entire set, as indicated by block 1114.

Figure 12:
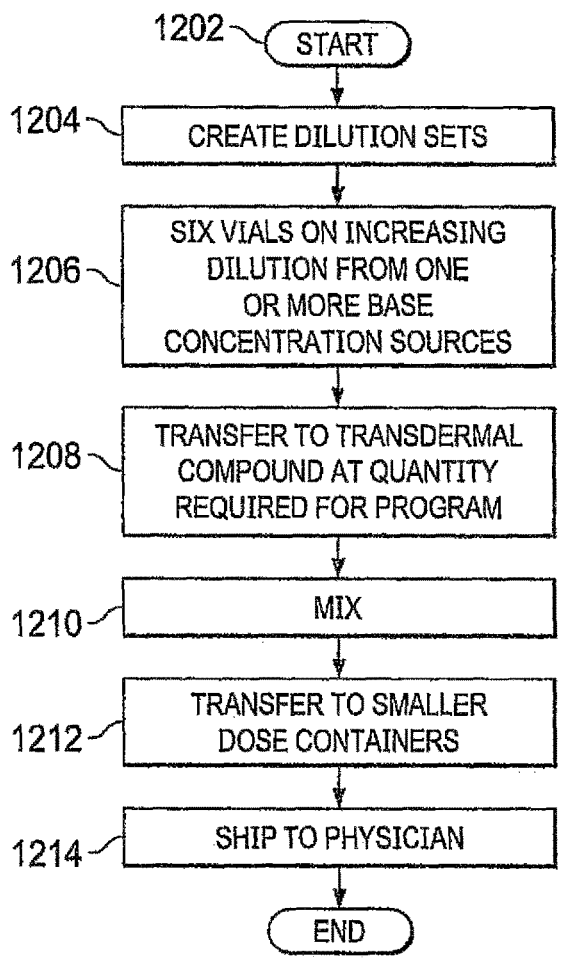

Referring now to FIG. 12, there is illustrated a flowchart for the operation of creating the dilution sets. This is initiated at a block 1202 and then proceeds to a block 1204 to create the dilution sets. This is facilitated by providing six vials of a saline solution into which a predetermined amount of allergen at a defined concentration level can be introduced. This is described in detail with respect to FIG. 1, above. By introducing a small amount of concentrated allergen or allergens from base concentration vials into a first of the six vials, a first dilution level, the highest, is achieved. This is mixed and then a small amount of this concentrated allergen or allergens is then introduced into the next vial and so on until the last and sixth vial is created at the lowest and starter concentration level. These six vials require an initial dilutant level sufficient to provide enough diluted allergen or allergens to provide a single or multiple therapeutic doses. For example, if a physician designed a program wherein the first dosage level required an introduction of ½ mL of diluted allergen or allergens for a total of 10 doses over a first time period, that would require only 5 mL of total diluted allergen or allergens as an initial starting base. However, it should be understood that, in order to obtain 5 mL of diluted allergen or allergens, there would have to be larger than a 5 mL bottle, since some diluted allergen is pulled from one bottle to the next. Thus, typically, if 5 mL of diluted allergen or allergens was required, a 10 mL bottle would typically be utilized. This, of course, is up to the compound pharmacist. In any event, at the first dosage level, the compound pharmacist would have to provide a sufficient amount of diluted allergen or allergens at that starter concentration level to provide 10 doses. This operation is illustrated in block 1206. Once the six vials at the increasing dilution levels from the starter dilution level have been created, the diluted allergen or allergens for each of the sets is then transferred to a transdermal cream, as indicated by a block 1208. The transdermal cream may also contain other medications, such as imiquimod, or the other medications may also be mixed in along with the diluted doses or at a later time. As noted hereinabove, each dose will be defined as associated with a predetermined volume of transdermal cream. Thus, the amount of transdermal cream for the total number of doses required for a particular set will be defined and that amount of allergen or allergens at that concentration level then will be transferred to the carrier transdermal cream. This will then be mixed, as indicated by block 1210, to ensure that the number of doses introduced to the carrier is thoroughly mixed throughout the carrier. This is then transferred to, for example, smaller dose containers, possibly one for each dose. This is indicated by a block 1212.

The final set of dose containers, there being a predetermined amount of doses for each concentration level, will be then shipped to the physician, as indicated by block 1214.

Figure 13:
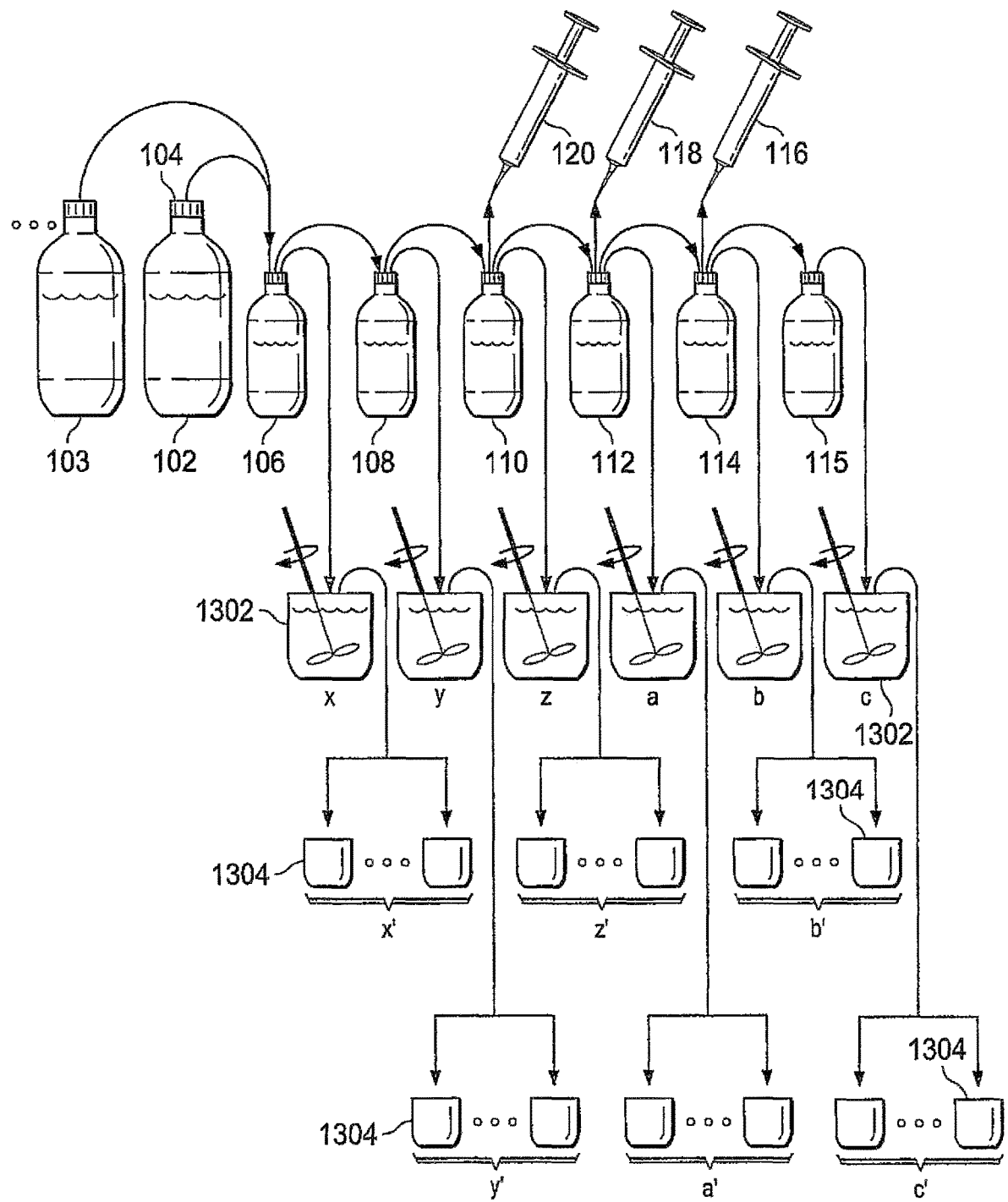

Referring now to FIG. 13, there is illustrated a diagrammatic view of the embodiment of FIG. 1, wherein there is added a second base concentration vial 103. This is indicative of at least two allergens being introduced into the program, it being understood that there could be more. The first and highest concentration or maintenance concentration vial 106 is first created with a small amount of allergen from each of the base concentration vials 103 and 102. If, for example, the vial 106 were a 10 mL vial, and the concentration level to be achieved in the vial 106 required there to be one half milliliter each from vials 103 and 102, then the initial saline solution or the such (there can be multiple dilutant carriers) would have to be initially at a 9 mL level. Thereafter, the predetermined amount of diluted allergens would have to be extracted from each vial in successive steps until the sixth vial 115. As noted hereinabove with respect to the embodiment of FIG. 1, these concentration levels are defined from the initial concentration level of the base allergen or allergens, and all that is defined by the compound pharmacist is the amount or number of doses that is required and the concentration level associated therewith. Typically, the concentration level for the starter dose in the vial 115 is defined by the physician and this defines what the higher concentration levels will be, this being a traditional method.

The next step is to provide a plurality of containers 1302 having a transdermal carrier material. This is at a defined volumetric level such that a particular number of doses from each vial 106-115 can be disposed therein. It may be that the physician only requires a certain number of doses for each set and these doses may be different. Thus, the compound pharmacist may place only 10 doses in the container 1302 associated with the vial 115 and 20 doses in the container 1302 associated with the vial 106. Thus, the compound pharmacist must determine the amount of transdermal cream associated therewith, assuming that each dose is associated with a predetermined amount of transdermal cream. This container 1302 could be sterilized and shipped to the physician in that form, thus requiring the physician to then open the container, creating an unsterile environment and then reuse it multiple times. Alternatively, the transdermal cream could be dispensed into smaller single dose containers 1304 for each set. As noted in FIG. 13, there are six final sets x', y', z', a', b' and c' for the respective vials 106-115. Each of these sets can have a different number of doses associated therewith and, thus, a different number of small containers. These can be small round containers or these could even be tubes. The object is that each of these is sterilized, such that dispensing of a single dose requires opening of the small container, resulting in an unsterile environment and an application of the transdermal cream therein to administer a single dose. Thus, there is no reuse of the particular container, resulting in the possibility of further bacterial contamination of transdermal cream. With a single dose container, the time between opening the container and use is short, thus minimizing the possibility of bacterial contamination.

Figure 14:
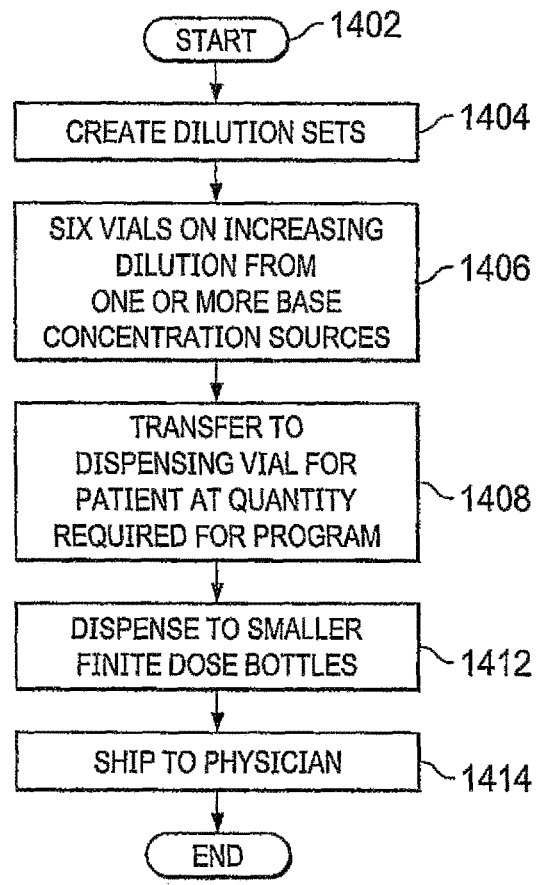

Referring now to FIG. 14, there is illustrated a flowchart for the operation of creating the dilution sets. This is initiated at a block 1402 and then proceeds to a block 1404 to create the dilution sets. This is facilitated by providing six vials of a saline solution into which a predetermined amount of allergen at a defined concentration level can be introduced. This is described in detail with respect to FIG. 1, above. By introducing a small amount of concentrated allergen or allergens from base concentration vials into a first of the six vials, a first dilution level, the highest, is achieved. This is mixed and then a small amount of this concentrated allergen or allergens is then introduced into the next vial and so on until the last and sixth vial is created at the lowest and starter concentration level. These six vials require an initial dilutant level sufficient to provide enough diluted allergen or allergens to provide a single or multiple therapeutic doses. For example, if a physician designed a program wherein the first dosage level required an introduction of ½ mL of diluted allergen or allergens for a total of 10 doses over a first time period, that would require only 5 mL of total diluted allergen or allergens as an initial starting base. However, it should be understood that, in order to obtain 5 mL of diluted allergen or allergens, there would have to be larger than a 5 mL bottle, since some diluted allergen is pulled from one bottle to the next. Thus, typically, if 5 mL of diluted allergen or allergens was required, a 10 mL bottle would typically be utilized. This, of course, is up to the compound pharmacist. In any event, at the first dosage level, the compound pharmacist would have to provide a sufficient amount of diluted allergen or allergens at that starter concentration level to provide 10 doses. This operation is illustrated in block 1406. Once the six vials at the increasing dilution levels from the starter dilution level have been created, the diluted allergen or allergens for each of sets is then transferred to a vial, or to a transdermal cream, as indicated by a block 1408. As noted hereinabove, each dose will be defined as associated with a predetermined administrable volume. Thus, the amount diluted antigen or antigens for the total number of doses required for a particular set will be defined and that amount of allergen or allergens at that concentration level. This is then transferred to, for example, smaller dose containers, possibly one for each dose. This is indicated by a block 1412.

The final set of dose containers, there being a predetermined amount of doses for each concentration level, will be then shipped to the physician, as indicated by a block 1414.

Figure 15:
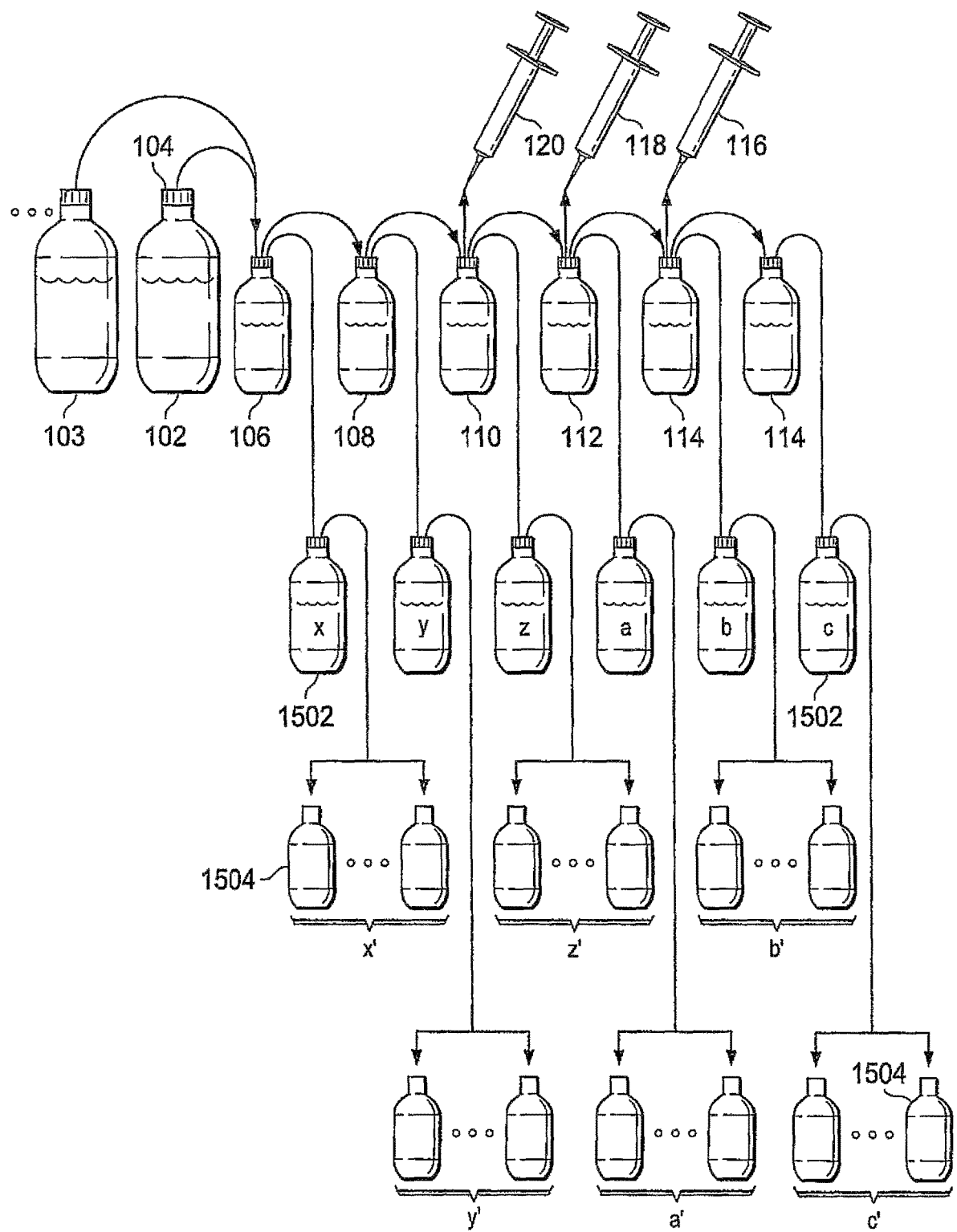

Referring now to FIG. 15, there is illustrated a diagrammatic view of the embodiment of FIG. 1, wherein there is added a second base concentration vial 103. This is indicative of at least two allergens being introduced into the program, it being understood that there could be more. The first and highest concentration or maintenance concentration vial 106 is first created with a small amount of allergen from each of the base concentration vials 103 and 102. If, for example, the vial 106 were a 10 mL vial, and concentration level to be achieved in the vial 106 required there to be one half milliliter each from vials 103 and 102, then the initial saline solution or the such (there can be multiple dilutant carriers) would have to be initially at a 9 mL level. Thereafter, the predetermined amount of diluted allergens would have to be extracted from each vial in successive steps until the sixth vial 115. As noted hereinabove with respect to the embodiment of FIG. 1, these concentration levels are defined from the initial concentration level of the base allergen or allergens, and all that is defined by the compound pharmacist is the amount or number of doses that is required and the concentration level associated therewith. Typically, the concentration level for the starter dose in the vial 115 is defined by the physician and this defines what the higher concentration levels will be, this being a traditional method.

The next step is to provide a plurality of containers 1502 for receiving the proper amount of diluted antigen or antigens representing number of doses for a particular set. This is at a defined volumetric level such that a particular number of doses from each vial 106-115 can be disposed therein. It may be that the physician only requires a certain number of doses for each set and these doses may be different. Thus, the compound pharmacist may place only 10 doses in the container 1502 associated with the vial 115 and 20 doses in the container 1502 associated with the vial six. This container 1502 could be sterilized and shipped to the physician in that form, thus requiring the physician to then open the container, creating an unsterile environment and then reuse it multiple times. Alternatively, the diluted antigen or antigens could be dispensed into smaller single dose containers 1504 for each set. As noted in FIG. 15, there are six final sets x', y', z', a', b' and c' for the respective vials 106-115. Each of these sets can have a different number of doses associated therewith and, thus, a different number of small single dose vials or containers. This small dose vial, compared to a multiple dose vial, allows dispensing of a single dose upon opening of the small vial, resulting in an unsterile environment once opened and upon application of a single dose. Thus, there is no reuse of the particular vial, resulting in the possibility of further bacterial contamination of the diluted antigen or antigens. With a single dose vial, the time between opening the vial and use is short, thus minimizing the possibility of bacterial contamination.

Referring now to FIG. 16, there is illustrated an overall therapeutic process flow for administering the therapeutic program to a particular patient, with a particular and defined program that is tailored specifically to that particular patient. This, as described hereinabove, is result of the testing and the design of the program for that particular patient and the subsequent manufacture and supply of the dilution sets for that particular patient in accordance with the design.

Initially, there are provided a plurality of dilution sets, each of the sets associated with a particular concentration level. These are defined as dosage sets D1, D2, D3, D4, D5 and D6. This defines a complete program, noting that each dosage set can have a different number of individual dosages associated therewith. This is defined as the program 1602. The physician then administers these in the following way. There is illustrated a timeline on the left side of the figure. The first dosage set D1 is administered in the office. If there were, for example, a requirement that five single doses be introduced subcutaneously to the patient at an interval of three days, that would require the patient to come into the physician's office every three days for five visits. In this manner, the physician can evaluate the patient to determine if there is any adverse reaction. This will continue for a period of time associated with that first dosage set D1. Thereafter, the second dosage set D2 will be administered over a second time period as defined by the number of doses in the dosage set D2 and the interval over which they need to be administered. For example, this dosage set could have six doses applied every two days, requiring the patient to come in for six visits separated by two-day increments. This will continue until the last dosage, D5 is to be applied in the office. At this point, the physician administers this last dosage to the patient at the prescribed interval for the number of doses associated with that particular dosage set. Once this has been completed, the last interval of time is entered, this being the maintenance interval. At this point, the last dosage set D6 is then packaged in a package 1610 and provided to the patient with instructions such that the patient can administer these doses themselves. It could be that these doses are provided in a transdermal cream or they are provided with injectable vials. It could be that there is provided a single vial with multiple doses with an indication that only a certain amount is to be utilized for each dose or there could be multiple vials, each vial associated with a single dose to provide a more sterile environment overall.

Referring now to FIG. 17, there is illustrated a diagrammatic view of the overall system for transferring NDC's between systems. The NDC, or National Drug Code, is a unique 10-digit, 3-segment number. It is a universal product identifier for human drugs in the United States. The code is present on all nonprescription (OTC) and prescription medication packages and inserts in the U.S. The 3 segments of the NDC identify the labeler, the product, and the commercial package size. The first set of numbers in the NDC identifies the labeler (manufacturer, repackager, or distributor). The second set of numbers is the product code, which identifies the specific strength, dosage form (i.e., capsule, tablet, liquid) and formulation of a drug for a specific manufacturer. Finally, the third set is the package code, which identifies package sizes and types. The labeler code is assigned by the FDA, while the product and package code are assigned by the labeler.

For example, the NDC for a 100-count bottle of Prozac 20 mg is 0777-3105-02. The first segment of numbers identifies the labeler. In this case, the labeler code "0777" is for Dista Products Company, the labeler of Prozac. The second segment, the product code, identifies the specific strength, dosage form (i.e, capsule, tablet, liquid) and formulation of a drug for a specific manufacturer. In our case, "3105" identifies that this dosage form is a capsule. The third segment is the package code, and it identifies package sizes and types. Our example shows that the package code "02" for this bottle of Prozac identifies that 100 capsules are in the bottle. The FDA maintains a searchable database of all NDC codes on their website. This is illustrated in FIG. 17A.

The NDC codes are unique codes that are applied for and assigned to specific individuals to be associated with specific products. Each manufacturer of allergens, for example, has a unique NDC associated with the product that they provide, which is assigned to that manufacture for that product based upon their applying for such. The manufacturer, therefore, has full ownership of that NDC. In order for that NDC to appear in a database with the associated information the approval of that manufacture is required. For example, a manufacturer of a well-known drug will provide information to the database and populate that database and the record associated with that NDC with the information regarding that product associated with that NDC but they will also define what the AWP is for that product. It is the manufacturer, not the person that controls the NDC of the manufacturer, that controls what is in database, including the AWP. Additionally, it should be noted that a distributor could actually apply for an NDC and could populate or associate with that NDC information regarding a particular product. They could actually place this NDC that they own, this being a unique NDC, in a database with another NDC, a different and unique NDC, that will be associated with basically the same product. This, of course, would provide some NDC contention within the database which is to be avoided if possible.

Thus, a manufacturer 1702 has associated there with its own proprietary database to store their NDCs. This can be provided to a central control center 1706. The central control center 1706 desires to have access to these NDCs of the manufacturer 1702. This is the primary reason that these NDC's do not exist in any other database. Typically, the central control center 1706 would have some type of contractual relationship with the manufacturer 1702 for the purpose of maintaining some type of exclusivity with respect to the manufacturer's NDC. Thereafter, these NDC's are stored in a central control database 1708. In this database 1708, the central control 1706 can modify the information. Primarily, the main aspect that they had is the AWP. This allows the central control 1702 to control this AWP. There is, of course, the wholesale cost exactly charged for the product to an end user such as a pharmacist, but the AWP is the benchmark price. This is not necessarily the price that the pharmacist, for example, will charge to the customer but, rather, it is the benchmark price. Further, this is not even the price that will be reimbursed to the pharmacist even if the pharmacist billed the customer for such. Thus, of course, this would not result in any type of price-fixing; rather, all that is controlled by the central control 1706 is the inclusion of AWP within the database. This AWP can be utilized by the reimbursing entities and the such for centering on a final reimbursement price.

In this disclosed embodiment, the data associated in with these venom derived allergens is then downloaded into a third party database 1710 associated with a third-party information provider. This information provider is one of many information providers that provide access through a network 1712 to a pharmacy 1714. It is noted, however, that the central control 1706 first confirms that none of the NDC's associated with any of the venom derived allergens is actually currently in the third party database 1710. Once these NDC's and their associated information and associated AWP's are stored in the third party database 1710, the central database 1708 has some control over both the information and the AWP associated with each of the NDCs. Thus, when a pharmacist receives a request from a physician to fill a prescription for a venom derived allergen for delivery to the physician, the pharmacist can access the third party database 1710 and determine that this is, in fact, in the database and is a reimbursable prescription.

Referring now to FIG. 18, there is illustrated a diagrammatic view of the third party database. This includes, in one column, NDC's, and a second column AWP's and in a third column information regarding the product associated with the NDC.

Referring now to FIG. 19, there is illustrated a flowchart depicting the initial operation of populating the database 1708. The central control 1706 initiates the process at a block 1902 and proceeds to block 1904 in order to receive the NDC from the manufacturer with the associated information regarding the associated product. This is one associated with product in the database of the control center 1706 and also with products controlled by the control center 1706. The control center 1706 is typically associated with some type of distribution center such that, in the information that they associate with the NDC in the database 1708, the control center 1706 and the entity associated therewith are the distribution arm for that product, i.e., this is where the product is ordered from by the pharmacist. The program then proceeds to a block 1908 wherein the AWP for that particular product and associated with that NDC is defined. This is a number that is set at whatever level is determined to be correct and appropriate by the control center 1706. There are a number of reasons for the price being set at any level. There is, of course, some cost of buying a product from the manufacturer 1702, the markup and expenses associated with the operation of the control center 1706, resulting in a wholesale price to the pharmacist. This wholesale price is not necessarily associated with the record that is stored in the database 1710. However, it is this information that is utilized in determining what the AWP will be for that NDC and associated product. A number of factors, of course, enter into that calculation, including practical knowledge of how the insurance industry reimburses for venom based allergens. After processing, the information is stored in the central control database 1708.

Referring now to FIG. 20, there is illustrated a flowchart depicting the transfer of data, which is initiated at a block 2004 and then proceeds to a block 2006 to access the third-party database through the network 1712. The program then flows to a function block 2010 to confirm that no NDCs in the control database 1708 exists within that third-party database 1710. The program then flows to a function block 2012 to populate the third-party database 1710 with information from the control database 1708, which, as described above, includes the information from the manufacture, information regarding the central control center 1706 as being a source of the product and the AWP for that product, all associated with the NDC for that product. The program that flows to a terminate block 2014.

Referring now to FIG. 21, there is illustrated a flowchart for the operation at the pharmacy. This is initiated at a block 2102 and then proceeds to a block 2104 wherein the pharmacist receives a request from a physician for a venom derived allergen. This might actually be presented to the pharmacist by a patient which desires to receive the venom derived allergen for dilution and processing by the pharmacist or it may in fact be an already diluted venom derived allergen that could be actually self-administered by the patient. The program then flows to a decision block 2106 to determine if the product is in stock. If the product is in stock, the program flows to a function block 2112 to check the database for reimbursement and, if not, the program flows to a block 2110 to process a stock item by whatever procedure the pharmacist utilizes. When checking the database, the pharmacist enters the NDC of the product, as indicated in a block 2114. The program then flows to a decision block to determine if the NDC is found, this being block 2116. If not found, the program exits and, if found, the program flows the function block 2118 wherein the pharmacist can view the AWP for that product. This gives the pharmacist some idea as to what might be reimbursable, but also, the insurer itself will illustrate some type of potential co-pay. This just indicates the amount that the patient will pay at the counter. The pharmacist then can enter an amount that the pharmacist will claim that they want to be paid for this particular product. It may be less than the AWP but not more than AWP. This, of course, is a function of what the pharmacist desires. This is indicated by block 2120. Thus, there is provided a third-party database 1710 having information contained therein, which is controlled by the central control center 1706 with respect to the venom derived allergens. Part of this is the AWP and part of it is the source for that venom derived allergen. The insurer has access to this information and can utilize it to adjudicate a claim. Information from the insurer can be linked to this database indicating a co-pay, for example. With respect to this, and insurer can indicate that it will pay the entire cost of the particular venom derived allergen or indicate what percentage of the venom derived allergen that it will pay for. Sometimes, it is just a co-pay. However, for some very expensive venom derived allergens, the insurer may over time decide that it only pays a small percentage of the venom derived allergen. This will be on an allergen-by-allergen basis. By allowing this third-party database 1710 to be controlled by the central control center 1706 with respect to the cost for the particular venom derived allergen, this allows central control center 1706 to control the adjudication of the particular venom derived allergen. The Program then flows to a function block to send a request to the third-party payee for reimbursement, as indicated by block 2122.

The process for adjudicating any claim requires that some entity or party has worked with the insurance company or the reimbursing entity to negotiate the particular reimbursement or any benefits that are provided. If the pharmacist is apprised of an AWP in the database for a particular venom derived allergen, they at least have a price that they can charge for the product. For example, if the pharmacist has a product on the shelf with an NDC any position writes a prescription for that venom derived allergen, the pharmacist just needs to know how much to charge the patient. By accessing the third-party database 1710, the AWP can be determined. However, that alone doesn't allow the pharmacist to determine whether benefits are associated with that particular venom derived allergen. In order to do that, there has to be some link between an adjudicating party or entity. The pharmacist can select the NDC and a field (not shown) that directs the pharmacist to an adjudicating party or entity to provide information as to benefits that are available. If such indicates that benefits are available, then the pharmacist knows that they can make a claim to this adjudicating party.

In the current disclosed embodiment, the central control center 106 maintains the adjudicating database. The central control center 1706 is responsible for interfacing with insurers and the such to provide these benefits. For example, if there are five major insurance companies that reimburse the pharmacist or even Medicare, the central control center 1706 will make the arrangements for reimbursement and allow the pharmacist to determine whether the patient, who may be associated with any of these reimbursement entities, can receive benefits. If, for example, the patient had insurance with Insurer A, and central control center 1706 had negotiated with Insurer A for certain benefits, this would be made available to the pharmacist. The benefits might provide for some type of co-pay which the pharmacist could charge to the patient and then the pharmacist could make a claim for the remaining value of the venom derived allergen to the adjudicating party, i.e., in this case the central control center 1706. The central control center 1706 would then process the claim and forward a check to the pharmacist. Since the central control center 1706 populated the third-party database 1710 with all of the NDCs, the central control center 1706 has exclusive rights to adjudicate these NDCs and the associated venom derived allergens. Thus, this unique link from the third-party database 1710 to the central control center 1706 allows all claims to be adjudicated therethrough because the central control center 1706 has exclusive control over these NDC for these venom derived allergens.

All of the NDCs, as noted hereinabove, or for venom derived and allergens that are to be dispensed to a patient are a single dose venom derived allergen. Thus, each of the NDCs that would be obtained by the manufacturer would be for single dose venom derived allergens rather than bulk venom derived allergens that are currently provided.

Figure 22:
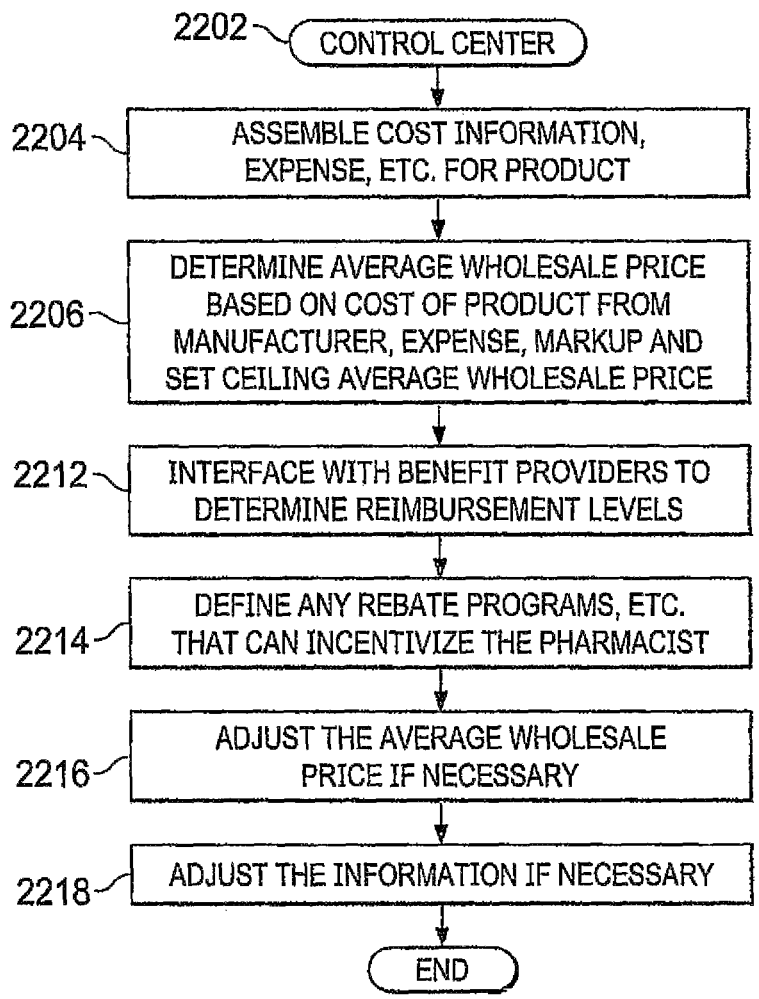

FIG. 22 illustrates a flow chart depicting the operation wherein the control center is able to determine the AWP by interfacing with the benefit providers. This is initiated at a block 2202 and then proceeds to block 2204 wherein the control center assembles the various cost information regarding the manufacturers cost to the control center, the expenses of storing the venom derived allergen at the control center, i.e., where the control center is the distributor and provider of the venom derived allergen, and what kind of markup or profit margin the control center expects to receive on a venom derived allergen. The program then flows a function block 2206 to determine the AWP. This AWP is based on the information retrieved in block 2204 and then a ceiling for the AWP is determined. This ceiling is a number that is arrived at by the control center based upon their knowledge of how the benefit providers reimburse pharmacists and the such. Since the AWP is a ceiling and the pharmacist cannot charge more than that, they provide a number that is a benchmark for the industry. By determining this benchmark, the insurance industry will typically center in on a lower reimbursable price, depending upon how valuable they think a particular venom derived allergen or the such is to the industry. For example, if they sold the product for $350 to the pharmacist, this being the wholesale price, they might set the AWP at $500. Over time, pharmacist may actually make a claim for only $450 which, at first, the insurance copies may reimburse. After a time, the insurance industry may come to the conclusion that this venom derived allergen is only reimbursable at a rate of $400.

The program then flows to a function block 2212 wherein a control center can interface with benefit providers to determine what the reimbursement levels are and, if necessary, adjust the AWP. However, they can also determine such things as rebate programs and incentives and the such that they can provide to the pharmacist, as indicated by a function block 2214. Since they control the database, they can also write information from the interface with that particular part of the database. The program then flows to a function block 2216 to adjust the AWP if necessary and then into a function block 2218 to adjust the information in the database if necessary.

The overall operation of initially testing patient at the physician's office, writing a script for the patient and completing the prescription by processing that script at a pharmacist location or some type of compounding pharmacy operation. In general, it must be noted that each script is very patient-specific; that is, in a system that is unique to testing for venom derived allergens, it is necessary to determine which of multiple antigens must be combined in a desensitization program. It may be that, for example, a prick test initially indicates that the patient is highly allergic to cat fur, dog care, various types of pollen, certain venoms, and the such. With a positive indication for these particular venom derived allergens, the physician can then determine which antigens need to be combined in some type of prescribed dosage regimen. Since there are so many venom derived allergens that can exist and since each patient is an individual, this combination can be somewhat daunting if the desire of the industry were to provide only that particular combination as a "drug" that has an NDC associated there with. This is practically impossible, of course.

Figure 23:
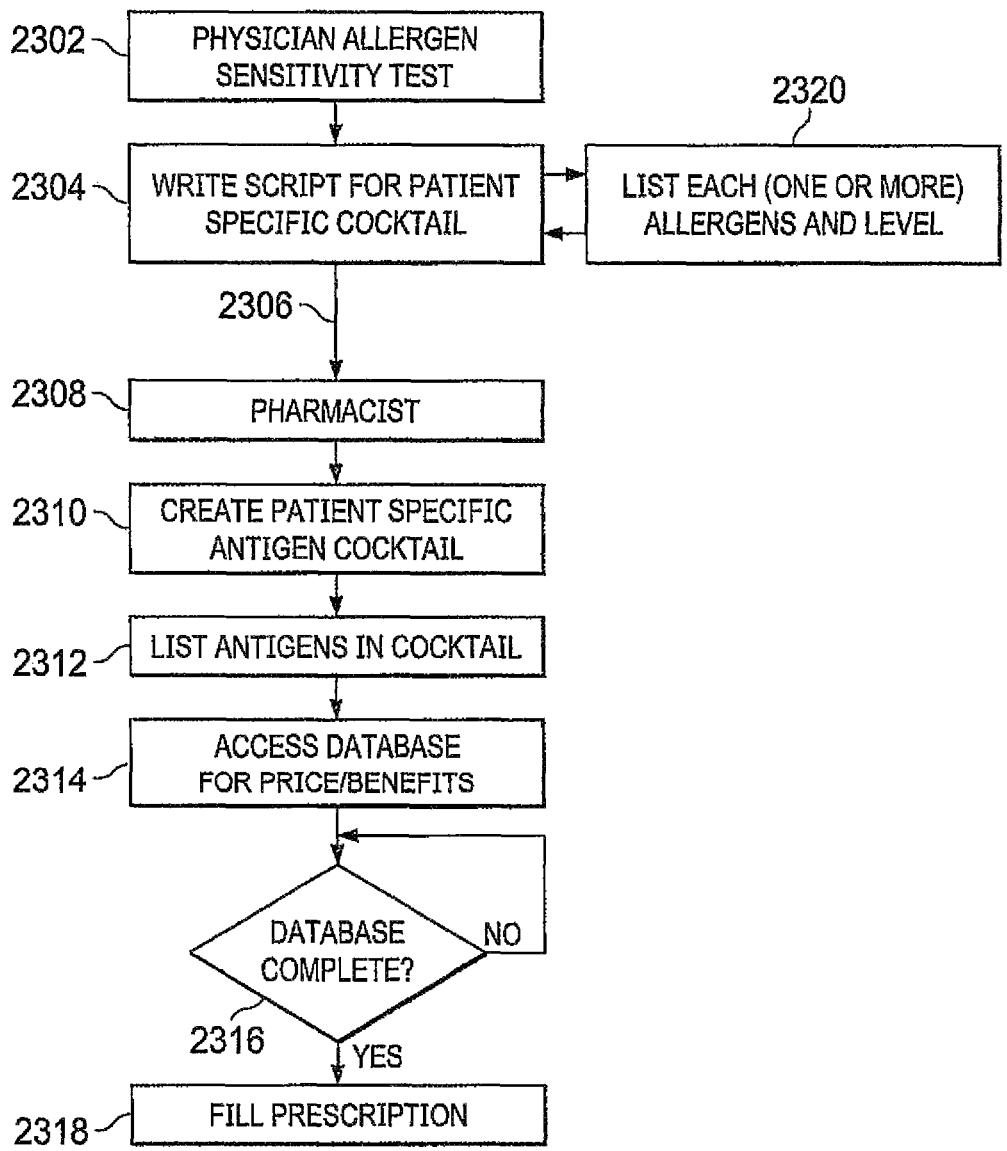

Referring now to FIG. 23, there is illustrated a flow diagram of the overall process of determining a particular combination of antigens to desensitize an individual and the regimen therefore. This is initiated at a block 2302 wherein the physician subjects the patient to what is known as a "prick" test. This prick test is a test whereby the physician introduces a small amount of venom derived allergens into a small area on the skin of an individual. There can be multiple spots that are arranged in a grid on, for example, a portion of the back of the patient. These allergen locations are recorded and then they are observed over a certain period of time. There is also typically some type of base allergen that is provided such as a hypoallergenic antigen and a hyper allergenic antigen such that there is an area that will result in no response and as an area that will result in a guaranteed response. Upon observation, areas that elicit a positive response indicate that the patient is sensitive to that particular allergen. It may be that the patient is very sensitive to certain of the allergens and just mildly sensitive to others. The physician then determines which of the allergens need to be included in a desensitization program. For example, if an individual in Texas showed a positive response to some allergen that rarely occurred in Texas, the physician might not include that in a desensitization regimen.

Once the regimen is set upon for a particular patient, a script is then written by the physician, as indicated by block 2304. This can be a script for a single venom derived antigen if that was all that was required for a desensitization program or it could be for a cocktail of multiple venom derived antigens. The physician will define the venom derived antigen or antigens that are to be included in the regimen, the dosage level and the carrier. For example, for the first desensitization level, the most diluted level of antigen will be utilized. Typically, the physician will require that the single venom derived antigen or cocktail of antigens be provided in a carrier such as saline or glycerol in a vial that will allow for a certain number of injections. It may be that the physician wants to prescribe for this first desensitization level a dosage that will allow for three injections per week for three weeks.

This script is then written and provided to the patient or it can be directly delivered to the pharmacist, as indicated by a path 2306 to a block 2308 indicating the pharmacist. The pharmacist then creates a patient-specific venom derived antigen cocktail, as indicated by block 2310. The pharmacist then lists the antigens that are contained within the cocktail, noting that there could be a single antigen. This is indicated at a block 2312 and then the pharmacist accesses the database for price and benefits. This is basically the Pharmacy Benefits Manager (PBM) database, which contains all of the drugs, etc., that are available for reimbursement. If the pharmacist, for example, looks up a particular antigen that was prescribed in the script and does not find it, this indicates that it is not something that can be reimbursed. If, however, this antigen exists within the database, it indicates both the AWP for that antigen and benefits associated there with. All of this is pre-populated within the database. However, with respect specifically to any antigen, the NDC for that antigen will only be associated with the base concentrate level. The script, however, is for a particular diluted dosage of that particular antigen and even a combination of multiple antigens at that particular dosage. This database is accessed at a block 2314 and then, after access is complete, as indicated by a decision block 2316, the prescription is filled at a block 2318. The operation of determining the particular AWP and benefits associated with any script for antigens at any dosage level, wherein the particular combination of antigens does not have particular NDC associated therewith nor does any antigen by itself have a particular NDC associated therewith, it is necessary to cross correlate this with an NDC that has an AWP associated therewith. Further, with respect to antigens specifically, the current NDC for any antigen is associated with the base concentrated material and this base concentrated material is too toxic to utilize at that concentration level. Thus, anything that is distributed to the patient will always be diluted from this base concentrated material. As will be described hereinbelow, it is always necessary to cross correlate any dosage level back to the NDC for the base concentrated material in order to determine benefits. Further, each of the scripts set forth by the physician will always have a list of each of the one or more allergens to which the patient exhibited a level of sensitivity thereto and the antigens associated there with. Further, the physician will determine the dosage level also. This is indicated by block 2320.

Figure 24:
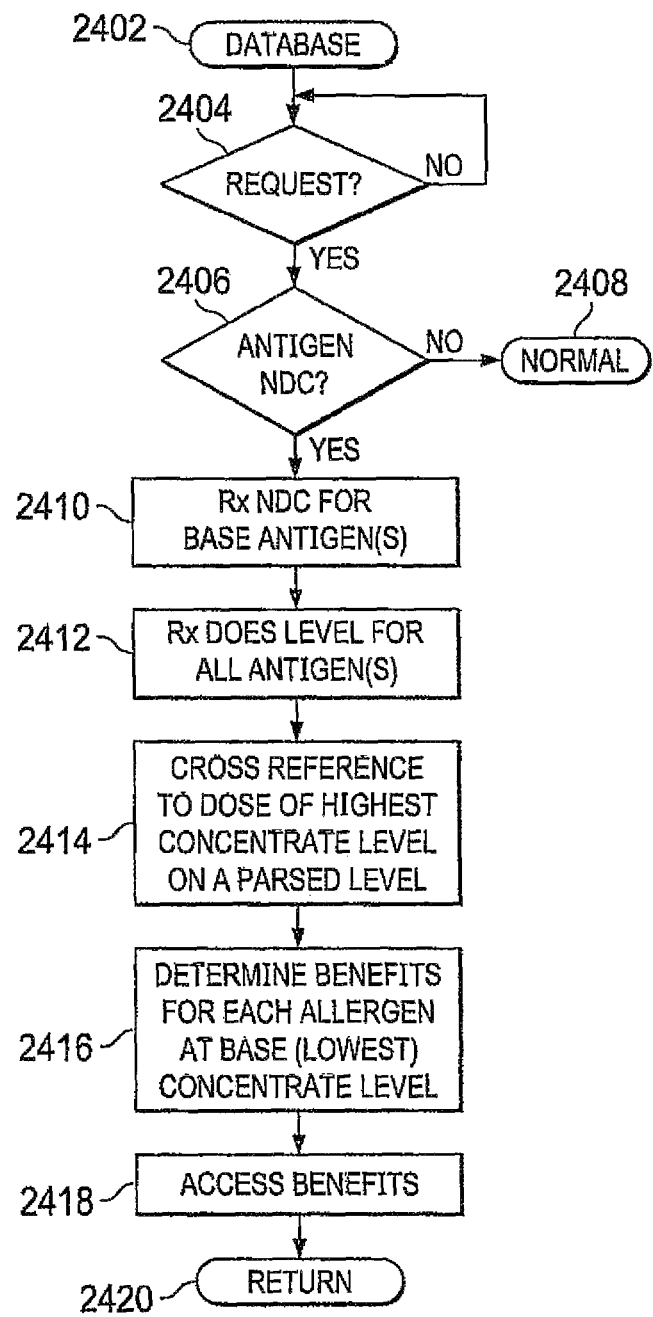

Referring now to FIG. 24, there is illustrated a flowchart depicting the operation of accessing the database, which is initiated at a block 2402 and then proceeds to a decision block 2404. The decision block 2404 determines whether a request for access has been received and, if so, the flowchart proceeds to a block 2406 to determine if the particular request of the PBM database is associated with that for an antigen. If not, the program will follow the "N" path to a block 2402 to proceed along the normal benefit determining process. This is not described herein. If, however, the request is for an antigen, this is a specific operation, since the only NDC that exists is for a base concentrated antigen that is too toxic to be directly distributed to a patient or for another dosage level that is to be diluted. Once an antigen NDC as indicated, the program flows to a block 2410 in order to receive the NDC for the base antigen or antigens and then to a block 2412 to receive the dose level for all of the antigens, as well as the carrier and the dilution procedure that is utilized. The program will then flow to a block 2414 in order to cross reference the particular dose level that was actually distributed to the patient to the dose of the highest concentrated level of the base concentrate material. This will be on a parsed operational level. This parsed operational level means that, for example, if 10 antigens were distributed in a cocktail, it would be necessary to cross reference the distribution of this particular dosage level to the actual material utilized from the NDC-carrying base concentrated level. If, for example, for a single base concentrated material that yielded an antigen in the cocktail mixed, required 1 mL out of a 50 mL bottle, the benefits for that one milliliter could be determined, as this is a "dosage" of the base concentrated level that is associated with an NDC. As indicated by a block 2416, the benefits can be determined for "each" allergen at a base or lowest concentrated level that is associated with an NDC. It is noted that an NDC might be provided for an already diluted level of a particular antigen. However, it is always necessary to determine what portion of the NDC-carrying material is utilized down to the final diluted level and then cross correlate this back to the NDC-carrying material at its particular dilutant level, this requiring some information as to the procedure for dilution, the carrier, etc. in order to adequately determine exactly how much of the NDC-carrying material was utilized. The program then proceeds to a block 2418 to then access the benefits and then to a block 2422 to end program.

Figure 25:
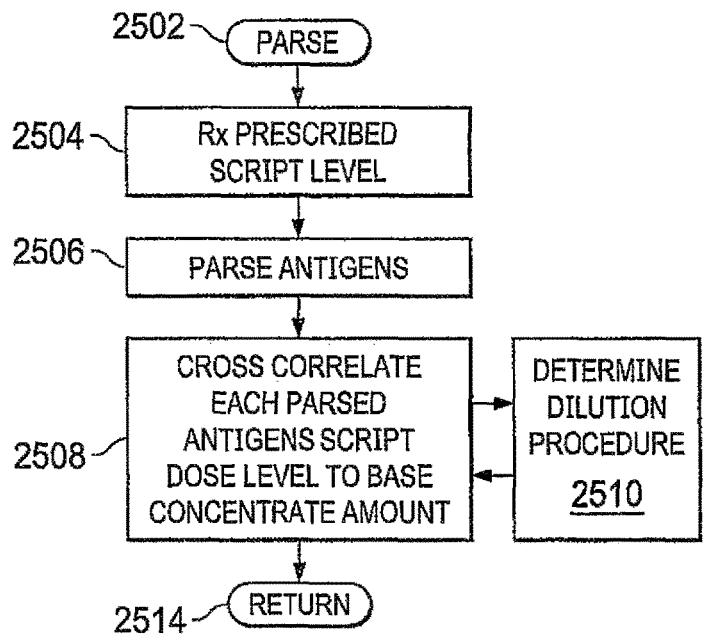

Referring now to FIG. 25, there is illustrated a flowchart for the parsing operation, which is initiated at a block 2502. The program then proceeds to a block 2504 in order to receive the prescribed script levels. The program then proceeds to a block 2506 in order to parse antigens in the cocktail to individual antigens (noting that a single antigen could be provided for). The program then flows to a block 2508 in order to cross correlate each of the parsed antigens and the script dose level back to the base concentrated amount, noting that this requires the carrier to be known, the procedure to be known for dilution. Since the script merely states that the most diluted level must be provided for, the pharmacist then to provide that particular antigen. The particular base concentrated antigen could be at different concentrated levels which would require a pharmacist to utilize one of multiple dilution procedures to obtain the final diluted level desensitization regimen. However, as will be described hereinbelow, it could be that physician prescribes a particular antigen in the cocktail that can be found in an antigen at a base concentrated level that contains multiple antigens. This is very common in the industry. For example, some companies deliver already mixed cocktails for various types of pollen. If the physician only prescribed one out of these types of pollen, then this procedure must be noted so that particular amount of base concentrated material, that can be reimbursed based upon its NDC, could be allocated. For example, if it were determined that 1.0 mL of the base concentrate pollen cocktail were required in order to get the prescribed amount of the one type of pollen, and this was from a 50 mL bottle, this would indicate a 1 mL dosage of the base concentrate level, but this would be divided by the number of particular antigens that are in the base concentrate material. If there were, for example, ten antigens contained in the cocktail, then this would be divided such that only $\frac{1}{10}^{th}$ of the dosage would be applied to benefits. That is, a 50 mL bottle would be considered as containing, assuming that the starting dosage is always 1 mL or any deleting process, as having 500 dosages of individual antigens. This, of course, requires knowledge of the dilution procedure, as indicated by a block 2510. Once the crosscorrelation is complete, the program proceeds to a return block 2514.

Figure 26:
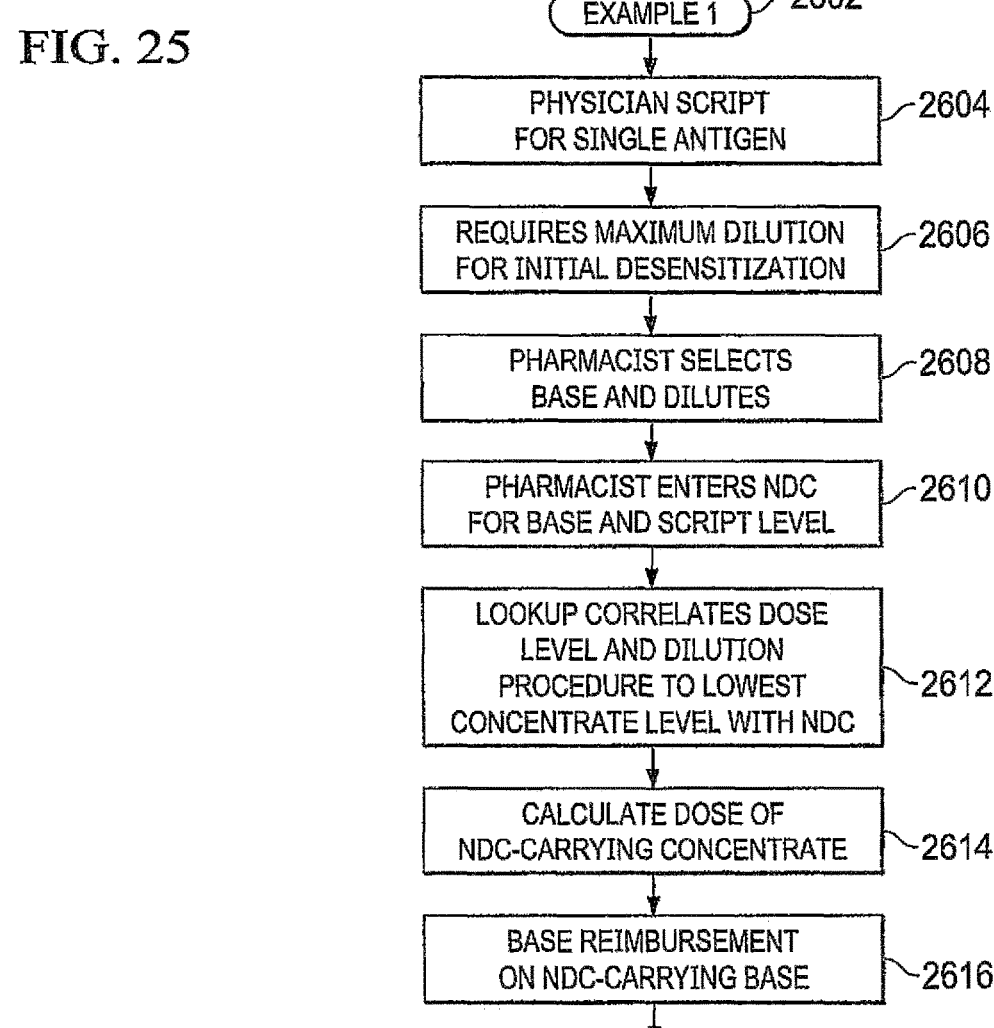

Referring now to FIG. 26, there is illustrated a flowchart depicting one example of the generation of a script for a single antigen and filling of that fiction based on that script and getting reimbursed therefor. This is initiated at a block 2602 and then proceeds to a block 2604 in order to prepare the physician script for a single antigen. The program then flows to a block 2606 in order to define the requirements of the maximum dilution for the initial desensitization. The physician defined at which level the script is written for. For example, the physician sets forth a regimen. This regimen defines six levels of dilution of a defined NDC base concentrate antigen, each level of dilution are required for a predetermined amount of time. For example, the most diluted level might be required to be administered in three doses per week for three weeks for total of nine doses. The first script would require the pharmacist to deliver to the patient a vial containing nine doses at that diluted level of the at least a single antigen. The physician could then require the second higher level to be provided over the course of one week at three doses per week. This might require a second script to be filled by the pharmacist or, alternatively, the pharmacist could fill that script that same time and maintained that particular vial on the shelf for distribution to the patient at a later time, all of this depending upon the script provided by the physician. Of course, the physician could require the patient to come into the office for observation and then write another script. This would be a separate and distinct operation and prescription which would be independently associated with a different set of benefits possibly.

After the dilution level is determined for the initial desensitization or at any level in the desensitization regimen, the program flows to a function block 2608 wherein the pharmacist selects concentrate antigen and then goes to the dilution process required in order to achieve the desired diluted level. The program then proceeds to a function block 2610 wherein the pharmacist enters the NDC code for the base concentrate level and the script level. Basically, what the pharmacist does is enter the antigen name and the dosage level provided by script. The program then proceeds to a function block 2612 in order to perform a lookup in the PBM database for the particular antigen that is associated with the script. This lookup does a correlation, as will be described hereinbelow, to the lowest concentrate level having an NDC for that particular antigen. Knowing the dilution level and the procedure, it is possible to determine what amount of the NDC-carrying concentrate level for that particular antigen was utilized and then a reimbursement obtained therefor. This is indicated by the function block 2614 and 2616. The program then flows to an initial End block 2618.

Referring now to FIG. 27, there is illustrated a table for a single antigen and the overall crosscorrelation information. This is a relational database. In this table can be seen that there is provided a column for the NDC code which is populated for a particular antigen. This indicates the name of the antigen and also information associated there with. There is also a dilution procedure for multiple procedures that can be associated with administering this particular antigen. Since the NDC code is not associated only with the type of antigen but also the concentration levels, this will be associated with the dilution level to determine what the various dilutant levels are in the overall standard process. As noted, the base level is indicated by a dilutant level D1 or a base concentrate level there than provide five additional dilutant levels D2 through D6. Each one of these dilutant level columns has associated there with a particular range of dilutant levels. As indicated by example, there are levels 1 through 3 for each of diluted levels, with more possible. Therefore, if the most diluted level, D6 were selected and that the procedure required that the dilutant level Z6 for the dilutant level column D6 were selected as the end dilutant level that was required by the physician in the script provided to the pharmacist, this would be what was put into the PBM system. However, there is no NDC associated with this particular antigen at this particular dilutant level. Therefore there must be some crosscorrelation back to column D1 for the base concentrate level, which column has an NDC associated there with. If the final dilutant level was Z6, this could be cross correlated back within the same row to the dilutant level Z1 of the base concentrate. However, although not shown, there could actually be multiple rows associated with the dilutant level Z6, one for each dilution procedure. Thus, the crosscorrelation from the antigen at a dilutant level back to the amount of bass constitute antigen required to process through the diluting procedure requires knowledge of the diluting procedure. This is illustrated in FIG. 27A, wherein each column for the dilutant level D6 has three procedures such that there are provided three different amounts of the base extract that would be required, Z1, Z1' and Z1". For example, it might be that this requires corresponding levels of 0.8 mL, 1.0 mL or 1.1 mL for those three different levels in order to accommodate the three different dilution procedures S1, S2 and S3. Thus, it is not just a mere crosscorrelation operation but, rather, and overall knowledge of the process that is required in order to determine how much actual product was utilized of the original base NDC-carrying antigen. Only when the amount of the base concentrate NDC-carrying antigen that is utilized is known can the actual dosage be determined. For reimbursement purposes, it is important to know whether 0.8 mL, 1.00 mL or 1.1 mL of the base concentrate NDC-carrying antigen is utilized. Reimbursement is calculated based upon this. However, all that is necessary for the pharmacist to do is to put in the end product that was generated and the procedure for coming up with that end product and relate that to the NDC of the antigen that was utilized.

Figure 28:
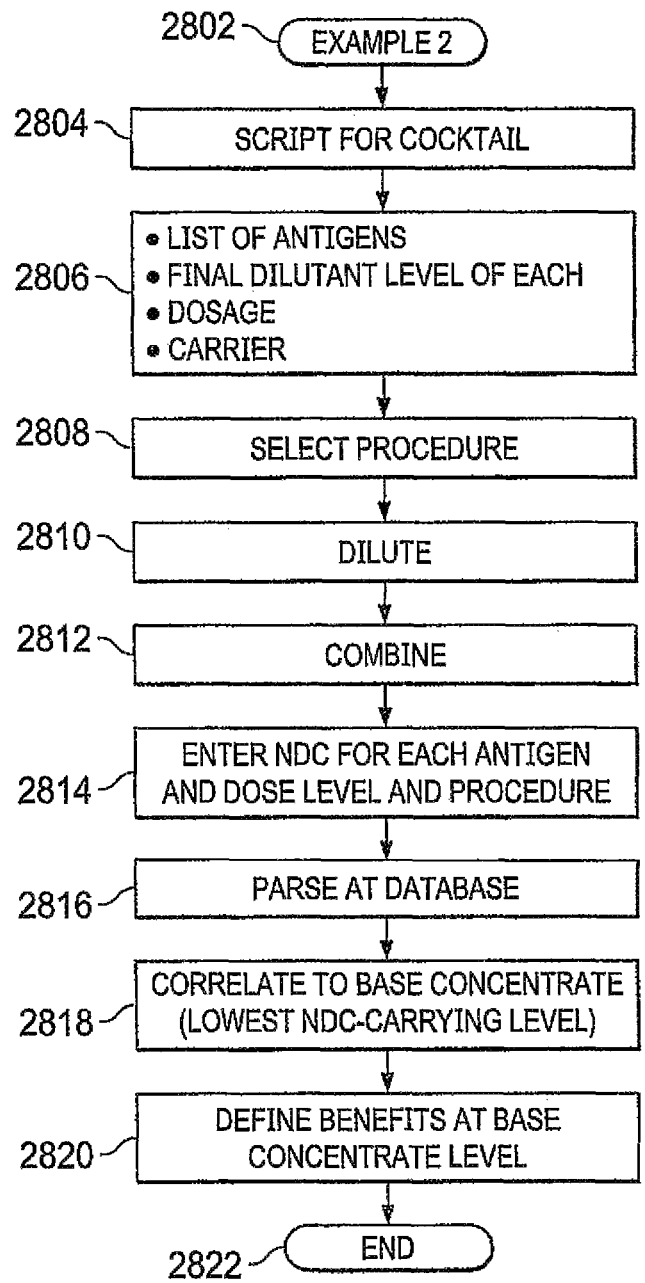

Referring now to FIG. 28, there is illustrated a flowchart for a second example for preparing a script for a cocktail, which is similar to the flowchart of FIG. 26. This is initiated at a block 2802 and then proceeds to a block 2804 to generate a script for a cocktail which is a patient-specific cocktail based upon a prick test performed. This is unique to that patient for that particular time. The program then proceeds to a function block 2806 in order to provide in that script a list of the antigens to be placed into the cocktail by the pharmacist, the final dilutant level of each, the dosage and the particular carrier. The program then flows to a function block 2808 in order to select the procedure that the pharmacist will utilize to provide this final diluted product with the prescribed number of dosages. This might be prescribed by the physician or it might be selected by the pharmacist. The program then flows to a function block 2810 wherein the pharmacist performs the dilution operation and then combines various antigens into the cocktail, at a block 2812. The program then proceeds to a function block 2814 wherein the NDC for each antigen is entered into the database, the dose level and the procedure. The program then proceeds to a function block 2816 to parse the particular antigens at the database, this parsing required in order to process each antigen in the database separately, as there must be a crosscorrelation back to each individual antigen, since only each individual antigen has an NDC associated there with. The program then proceeds to a function block 2818 in order to correlate the antigen back to the lowest concentrate NDC-carrying level, as described hereinabove with respect to the embodiment of FIGS. 26 and 27 and then to a function block 2820 in order to define the benefits and then to a function block 2822 in order to end the program, after the cocktail has been distributed to the end user such as the patient or the medical professional.

Figure 29:
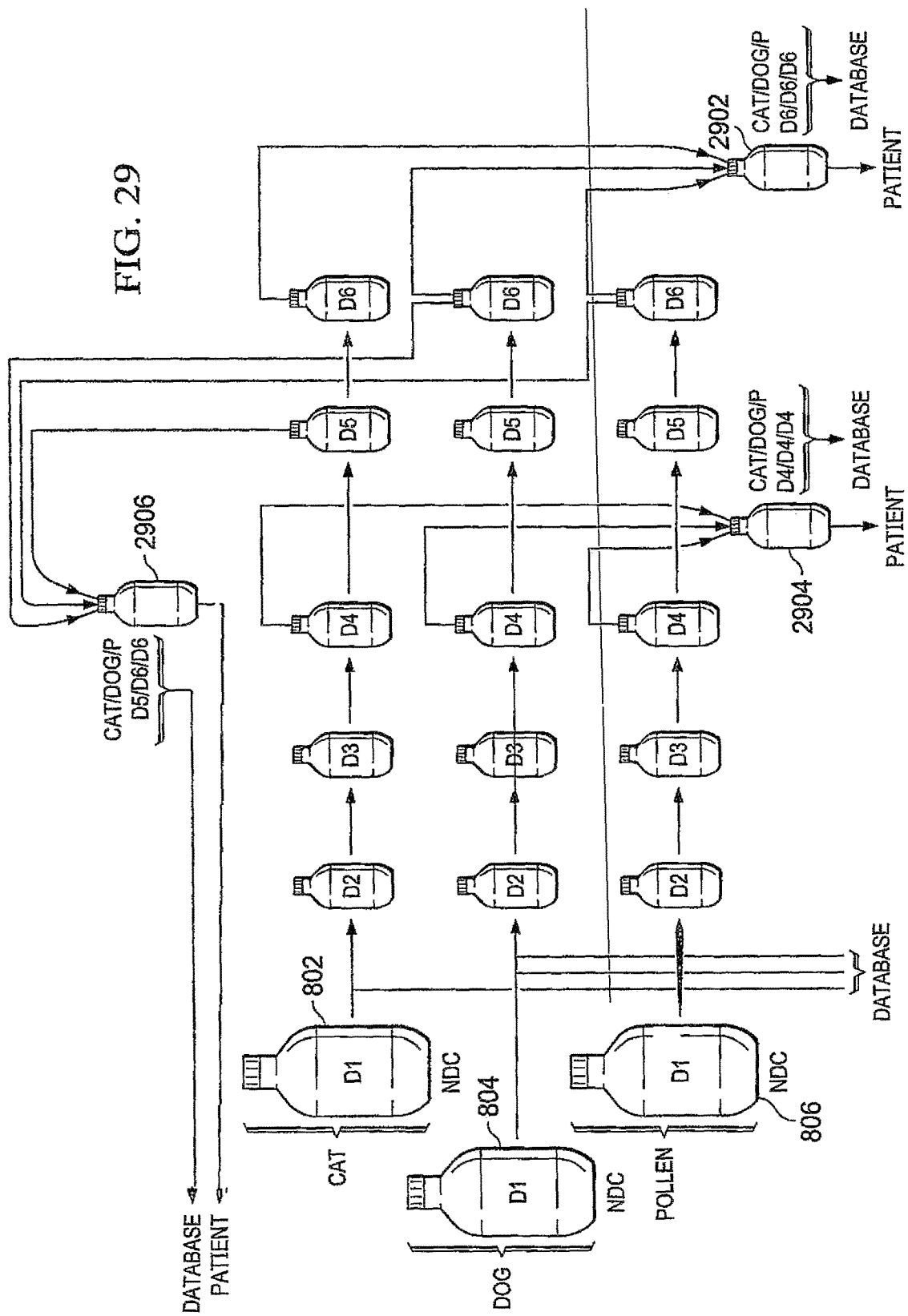

Referring now to FIG. 29, there is illustrated a process, which is similar to that described hereinabove, for creating a cocktail from three different base concentrate antigens 802, 804 and 806, referring hereinabove to the description with respect to FIG. 8. These are diluted down in five separate steps to a final dilution level D6. In a first operation, there is provided a final vial 2902 that receives the final dosage from each of the processes for diluting the initial base concentrate levels. It may be that each of the final vials D6 each have 5 mL contained therein. By containing no carrier material in the final vial 2902, 3 mL of each of the extracts can be placed therein resulting in a vial with 9 mL therein. If the physician prescribed the regimen to deliver a 1 mL dose of this concentrated level three times per week for three weeks, this would require nine doses and thus 9 mL of the cocktail. This overall process, for example, would require the pharmacist to understand each step of the dilution process to arrive at the final diluted. Thus, the pharmacist would indicate that there were three antigens in the final vial 2902 and that they were at the concentrate level D6/D6/D6. This would be provided to the PDM database. With this information alone, the system at the PDM database can cross correlate this back to the exact amount of base concentrate level lies for each of three base concentrate antigens 802, 804 and 806 utilized.

Alternatively, there is provided a vial 2904 which is the result of a different selection of cocktails from the D4 level. This, again, would have the three antigens in the concentrate level D4/D4/D4. This would again be provided to the PDM database which would then, based upon the dilutant level for each of the antigens and the procedure utilized to achieve that dilutant level to relate this back to the antigens utilized at the lowest NDC-carrying concentrate level. If, for example, this vial 2904 resulted in 9 mL of material but the physician only required three doses of 1 mL each for two weeks, this would only require 6.0 mL. The pharmacist might only dispense 6 mL out of the 9 mL to the patient or professional. Even though three doses were distributed or 6.0 mL, this 6 mL of final product of D4/D4/D4 of Cat/Dog/Pollen, for example, or a venom derived antigen, antigen has to be related back to the original antigen value.

In an alternate embodiment, there is a vial 2906 provided that has been provided where in it receives diluted antigens from slightly different vials. In this operation, the three antigens are D5/D6/D6 and this is provided back to the PDM database. Of interest is that all three vials 2902,2904 and 2906 will each be input to the PDM system with their procedure and the result will be that, for this example specifically, that the reimbursement be the same, as the starting dilutant will be identical. This is procedure specific and script specific, with the cocktail noted as being patient-specific.

Figure 30:
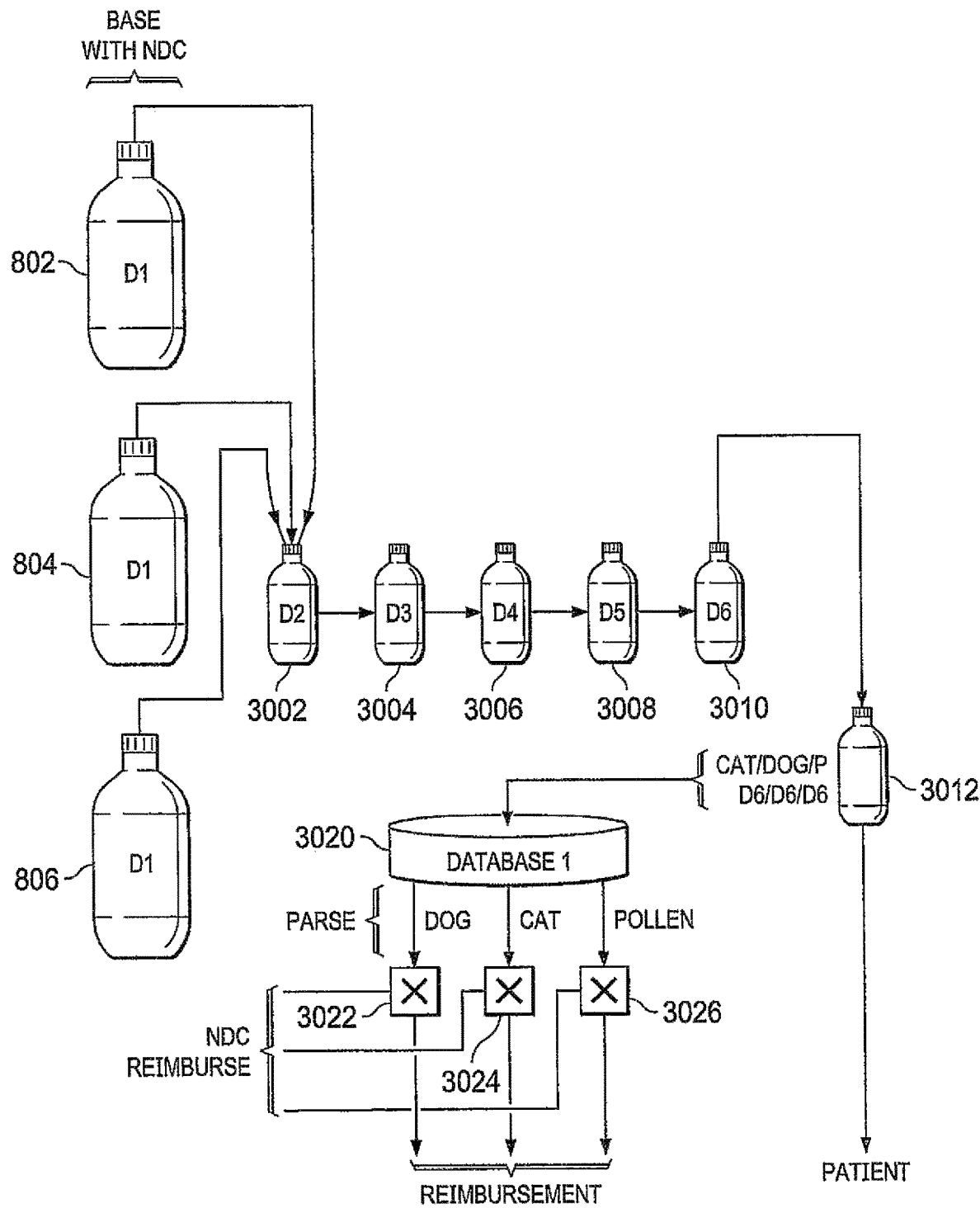

Referring now to FIG. 30, there is illustrated an alternate embodiment wherein each of the base antigens 802, 804 and 806 are subjected to a different procedure wherein each of the original starting amounts are input to a first diluting vial 3002 and are subsequently diluted through vials 3004,3006, 3008 and 3010 to a final vial 3012. This is then distributed to the patient. This final vial represents the dilution at the vial 3010, which is D6/D6/D6. This, along with this procedure, is then transferred to the PDM database, as indicated by block 3020, which is then parsed to the specific antigens and into a translator associated with each antigen, indicated by a "X" for the crosscorrelation operation, blocks 3022, 3024 and 3026 associated with the Dog, Cat and Pollen antigens, or venom derived antigens, which will then define the reimbursement. Each translation block 3022 will be associated with a reimbursement database for defined benefits associated with the particular antigen. Of course, it is important to know the amount of antigen that was actually utilized in the overall procedure which, again, requires knowledge of the final script dilutant level of the antigen delivered to the patient and procedure for obtaining that diluted level.

Figures 31A, 31B:
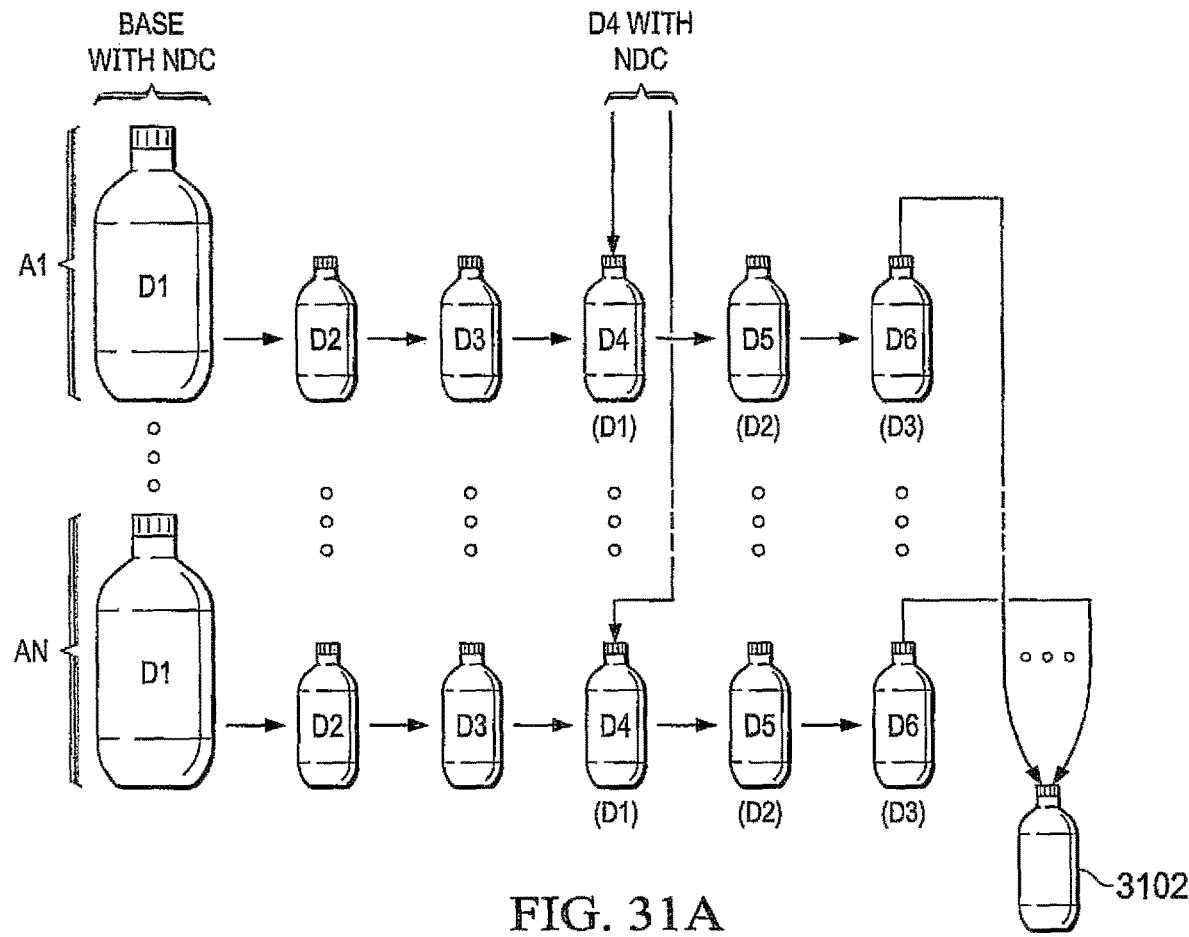

Referring now to FIG. 31A, there is illustrated a diagrammatic view of an overall process where in the NDC is associated with an intermediate level of dilutant. In this embodiment, the dilutant level D4 is illustrated as having an NDC associated there with, as well as the base concentrate level of. Thus, it is possible that the reimbursement and be defined back to this intermediate concentrate level. This is indicated in a table in FIG. 31B, wherein the table can have associated with original diluted levels D4, D5 and D6 crosscorrelation relationships with respect to the base concentrate level but, in this table, there are only three diluted levels required, the dilutant level for vial D4, the vial D5 and the vial D6. If the concentrate level at the final vial was X3 based upon the NDC code being at vial D4, all that would be required is to do a crosscorrelation back to the dilutant level required from the vial D4. This would be for each of the dilutant set was combined in a vial 3102 from each of the antigens in the script, this indicated as being the antigens A1-N.

Figure 32:
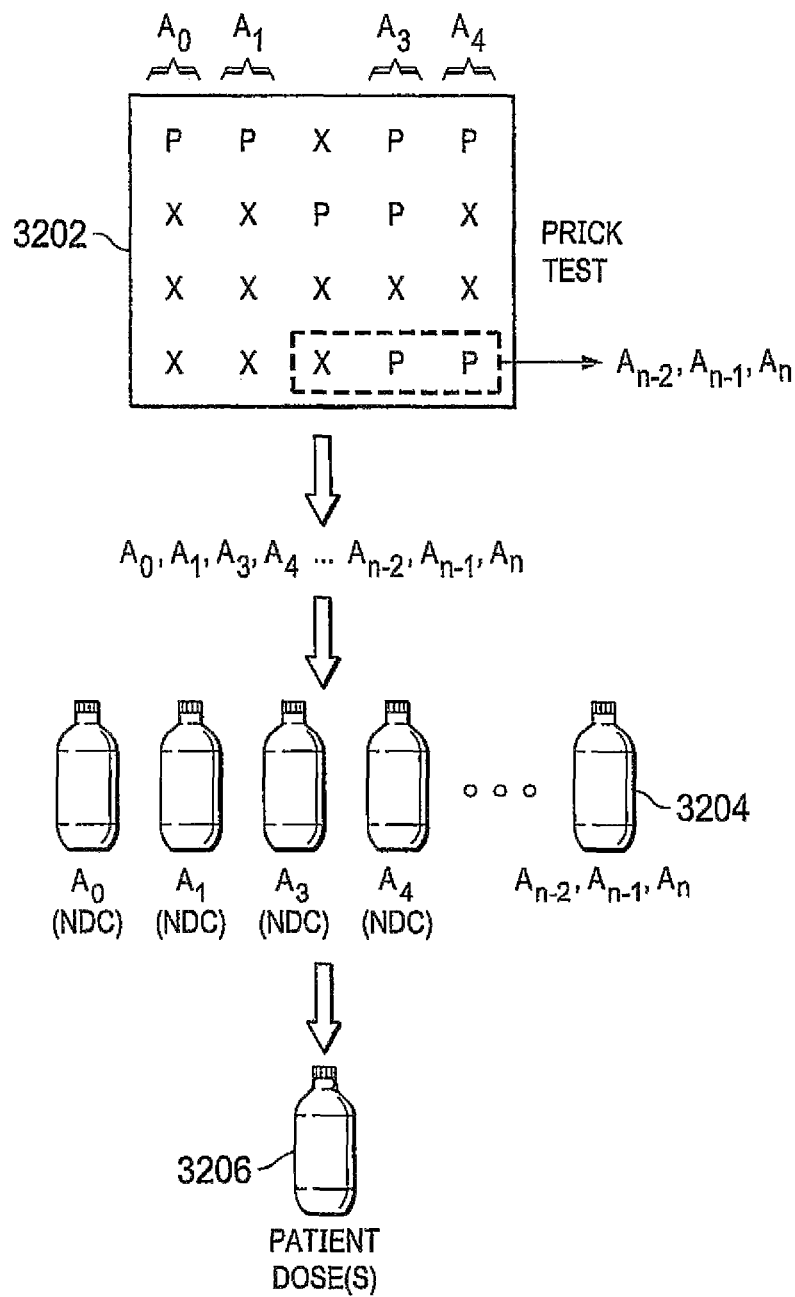

Referring now to FIG. 32, there is illustrated a process for mapping prick test to the script. As illustrated, there is provided a diagram of the prick test, indicated by a reference numeral 3202. This diagram 3202 indicates the locations of the particular allergens that were administered to locales on the person of the patient. This diagram illustrates the results with a "P" indicating a positive reaction and that an "X" indicating a negative reaction. Thus, the "P" indicates a sensitivity that must be considered in the script. Of interest is that the particular manufacturers of antigens might have a cocktail already existing in the base concentrate. This is illustrated with the bottom three test associated with antigens A(n−2), A(n−1) and AN. These are the last three antigens in the list. Of these, the last two are positive and the third for the last is negative. However, the script will have to include only the last two for the patient-specific script but the pharmacist only has the cocktail of all three available to them. Thus, the script will have a A0, A1, A3, A4 . . . , A(n−1) and AN as the antigens that are required for the desensitization regimen. This will be provided to the pharmacist which will then select NDC-carrying antigen bottles A0, A1, A3, A4 . . . , And finally a bottle 3202 containing A(n−2), A(n−1) and AN, wherein only A(n−1) and AN are required in script to fill the prescription. This is then processed to provide the final patient dosage in the cocktail in the vial 3204.

Figures 33A, 33B:
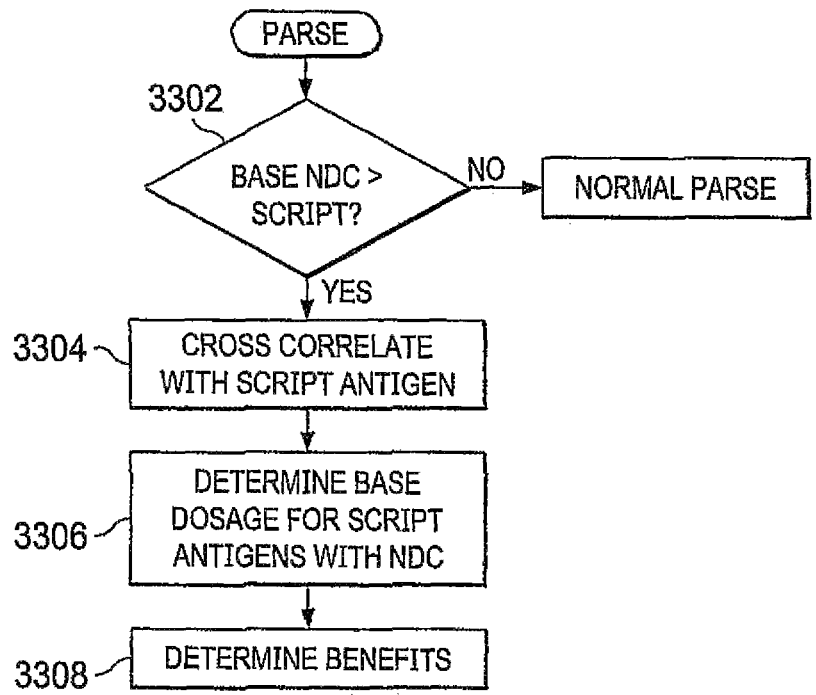

Referring now to FIG. 33A, there is illustrated a flowchart depicting the overall parsing operation before the operation of FIG. 32. In this operation, if the base NDC has a greater number of antigens than the script, a decision block 3302 will determine such and flow to a block 3304. The program will then flow to a function block 3306 in order to determine the base dosage for the script as required by and set forth by the physician of the antigens with the particular NDC, even though that NDC is associated with more than the antigens required by the script. The program then flows to a function block 3308 in order to determine the benefits. This is illustrated best with respect to the table of FIG. 33B. Here, it is illustrated that there are three procedures for providing the end dilutant level at the vial D6 for each of the antigens in the cocktail antigen vial 3204. If a certain amount of antigen is extracted from this particular vial 3204, it will contain all three antigens. At a particular concentrate level at the level D6, this will yield the necessary concentrated level of the two antigens desired even though the third antigen is included. Since the final dilutant level is known for the two prescribed antigens, they can be cross correlated back to the amount of antigen that was actually extracted. However, for example, if 3 mL of the extract in vial 3204 were extracted, this might represent a particular portion of a 100 mL bottle and, if all three antigens have been prescribed, this would be the basis for the reimbursement. However, if only two antigens were prescribed, only two thirds of that prescribed extract would be reimbursed. Thus, by utilizing known script at the known dilutant level, this can be cross correlated back via the standard procedure (or whatever procedure is utilized) to what was actually utilized of the NDC-carrying base concentrate material to actually derive the final prescribed and delivered antigen to the patient.

Figure 34A:
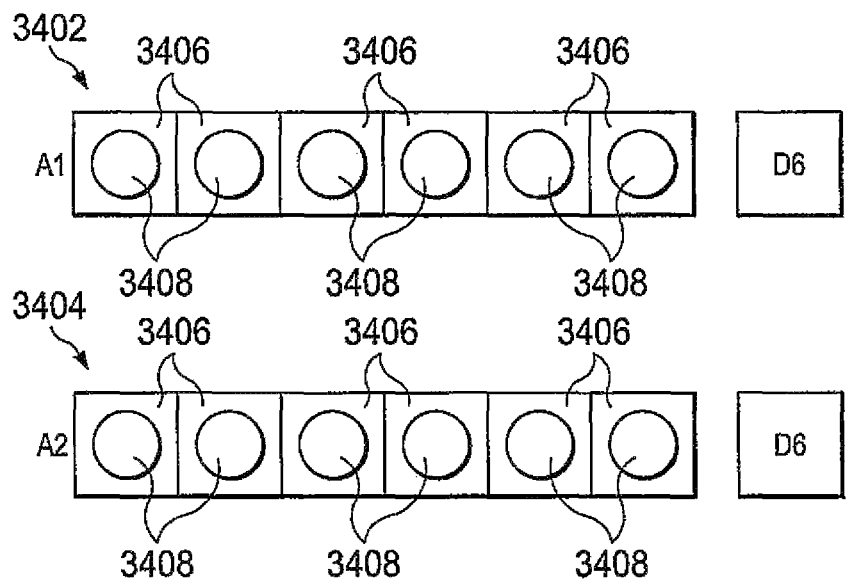
FIG. 34B illustrates a cross-sectional view of one embodiment of an antigen transdermal patch.

Referring now to FIG. 34A, there is illustrated a top view of one embodiment of single dose antigen and imiquimod transdermal patch sheets 3402 and 3404. In this embodiment, single dose antigen and imiquimod transdermal patch sheets 3402 and 3404 each correspond to a different antigen, A1 and A2, respectively, and each contain an amount of imiquimod, in order to deliver a cocktail of imiquimod and antigens at a prescribed dilutant level. Additionally, single dose antigen and imiquimod transdermal patch sheets 3402 and 3404 may each correspond to a particular dilutant level for the antigen, such as dilutant level D6. Each of the single dose antigen transdermal patch sheets 3402 and 3404 have a plurality of individual antigen specific single dose patches 3406, with each of the plurality of patches 3406 having an antigen carrier 3408 and each patch constituting a "single" dose of the associated antigen. The carrier 3408 may be a gel, such as a hydrogel, a cream such as that described herein, or another suitable carrier for an antigen. The carrier 3408 may have already included a single dose at a particular dilutant level of antigen, such as D6, or may only ship as the carrier with no antigen included, so that the antigen can later be added by someone such as a pharmacist. The carrier 3408 may also include a permeation enhancer. In the case of a hydrogel, the carrier may be produced using ingredients such as polyvinyl alcohol, sodium polyacrylate, acrylate polymers, and copolymers. Each of the plurality of patches 3406 may be cut from the sheet when a patch is needed. Antigen and imiquimod transdermal patch sheets 3402 and 3404 may thus be used for creating either single "single dose" antigen and imiquimod transdermal patches, or a single dose patch made up of the combination of antigens, such as both antigens A1 and A2, as will be described herein.

Figure 34B:
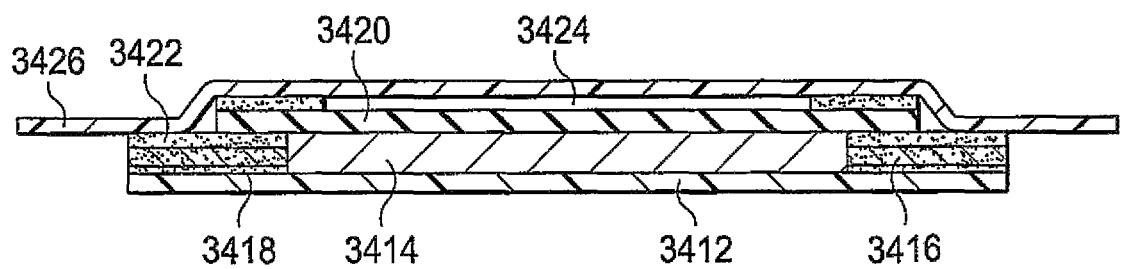

Referring now to FIG. 34B, there is illustrated a cross sectional view of one embodiment of a single dose antigen and imiquimod transdermal patch 3410. The single dose antigen and imiquimod transdermal patch 3410 may be one of the patches in the antigen transdermal patch sheets 3402 and 3404 described in FIG. 34A. The single dose antigen and imiquimod transdermal patch 3410 includes a back liner 3412. The back liner 3412 may be made of a material that is impervious to an antigen carrier 3414, and any antigen therein, used in the patch. The patch 3410 further includes a carrier platform 3416 upon which the antigen carrier 3414 is disposed. Upon creation of the patch, the antigen carrier 3414 may have a single dose of antigen at a prescribed dilutant level already contained within, or may later have an antigen added by someone such as a pharmacist for a single dose at a prescribed dilutant level. A first adhesive coating 3418 adheres the carrier platform 3416 to the back liner 3412. The carrier platform 3416 may be of a circular shape and may also have a recessed middle portion forming a cell that allows for the antigen carrier to be held within. The patch 3410 further includes a pharmaceutically diffusing cover 3420 that, when in use on a patient's skin, allows for the antigen to pass through into the patient's skin. The cover 3420 may be made of a tissue material, silicone, or some other porous material. The cover 3420 is held in place against the carrier platform 3416 by a second adhesive coating 3422. A third adhesive coating 3424 holds a peelable release liner 3426 over the cover 3420, to protect the contents of the patch. Once the patch is to be used, the peelable release liner 3426 is peeled away and the patch can then be applied to the skin, with the adhesive coating 3422 serving to adhere the patch to the skin. It is noted that the amount of antigen and imiquimod disposed in the patch will be a sufficient amount that, when released, will constitute a single dose "deliver" transdermally to the patent and, thus, more than an actual single dose of antigen will be disposed in the patch. The actual amount will vary depending upon the type of patch and the delivery mechanism.

Figure 35A:
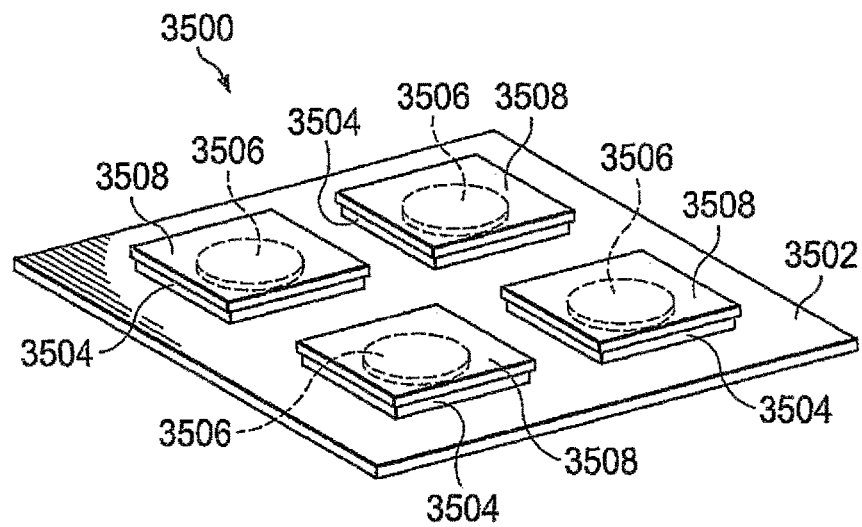
FIG. 35A illustrates a perspective view of one embodiment of a multi-antigen patch.
Figure 35B:
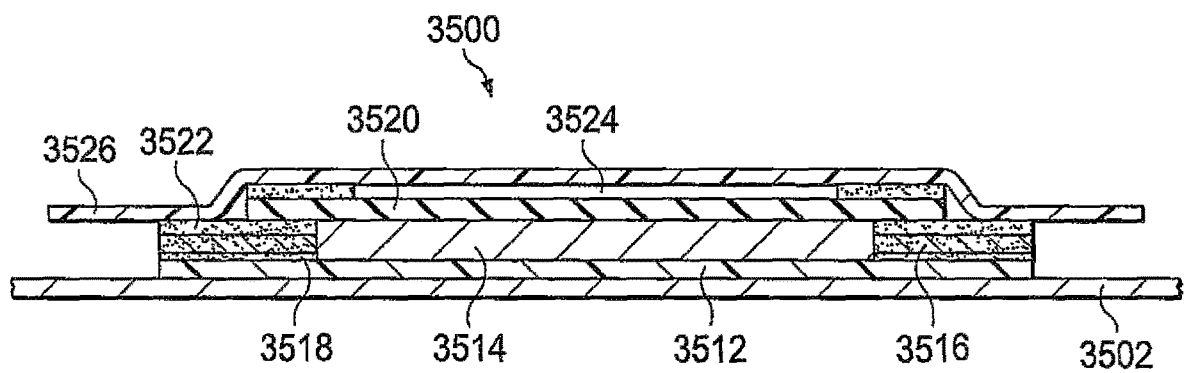
FIG. 35B illustrates a cross-sectional view of one embodiment of a multi-antigen patch.

Referring now to FIGS. 35A-B, there is illustrated one embodiment of a single dose multi-antigen and imiquimod patch 3500 at a particular dilutant level. The single dose multi-antigen and imiquimod patch 3500 includes a backing 3502 upon which multiple single dose antigen and imiquimod patches 3504, such as those described in FIGS. 34A and 34B, and each having an antigen carrier 3506, may be adhered to, in order to provide multiple single dose antigens in a single patch. The patches 3504 each also include a peelable release liner 3508. The backing 3502 may have designated spaces with adhesive coating for attaching each of the patches 3504, or the backs of the patches 3504 may have adhesive applied so they can be adhered to the backing 3502. In many embodiments, the patches 3504 are of a small enough scale that the single dose multi-antigen patch 3500 need not be bigger than a standard transdermal patch. The patch 3504 is identical to the patch described in FIG. 34B, except that they are attached to the backing 3502.

Figure 35C:
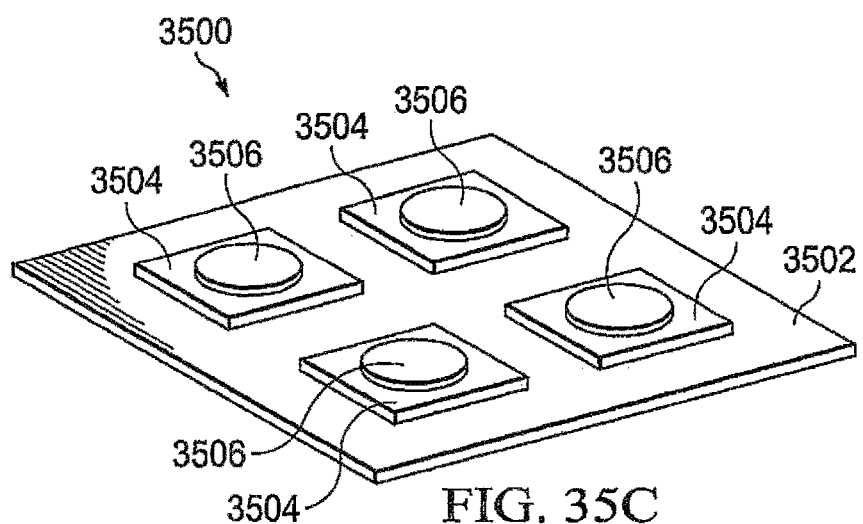
FIG. 35C illustrates a perspective view of one embodiment of a multi-antigen patch.
Figure 35D:
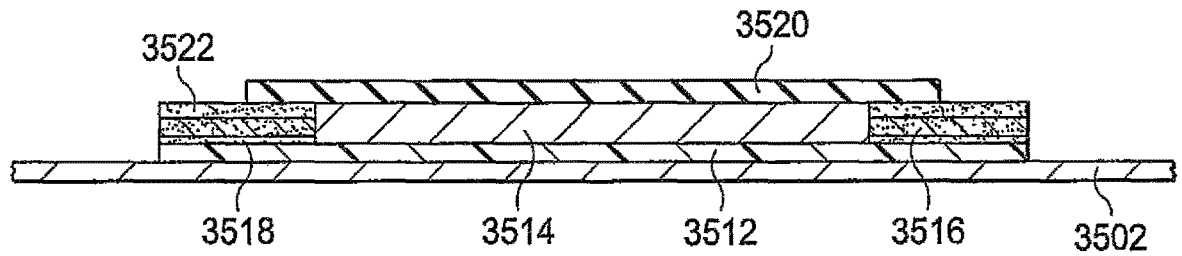
FIG. 35D illustrates a cross-sectional view of one embodiment of a multi-antigen patch.

Referring now to FIGS. 35C-D, there is illustrated the single dose multi-antigen (at a prescribed dilutant level) and imiquimod patch 3500 in the process of preparation. This will hereinafter be referred to as a "multi-antigen" patch, it being understood that each antigen is a single dose at a prescribed dilutant level. The multi-antigen patch 3500 now has had each of the peelable release liners 3508 removed from the patches 3504.

Figure 35E:
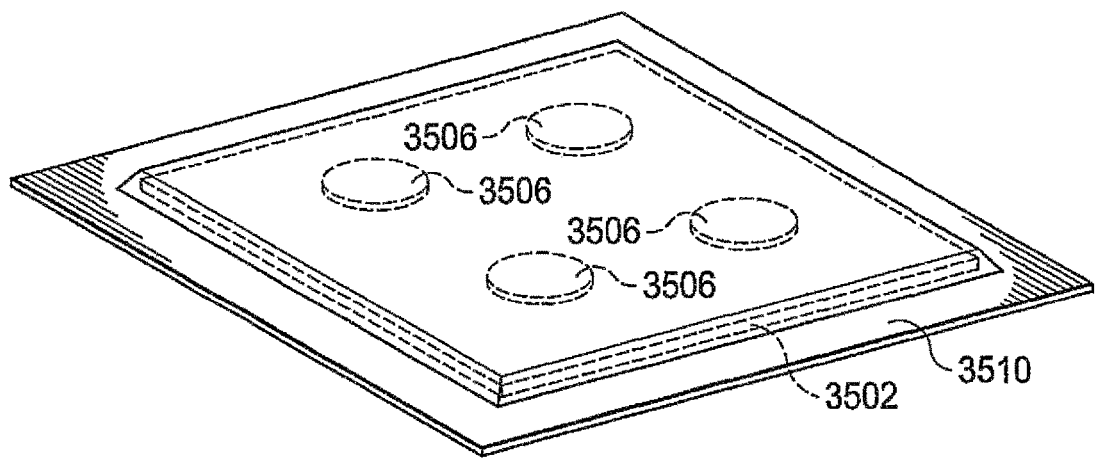
FIG. 35E illustrates a perspective view of one embodiment of a multi-antigen patch.
Figure 35F:
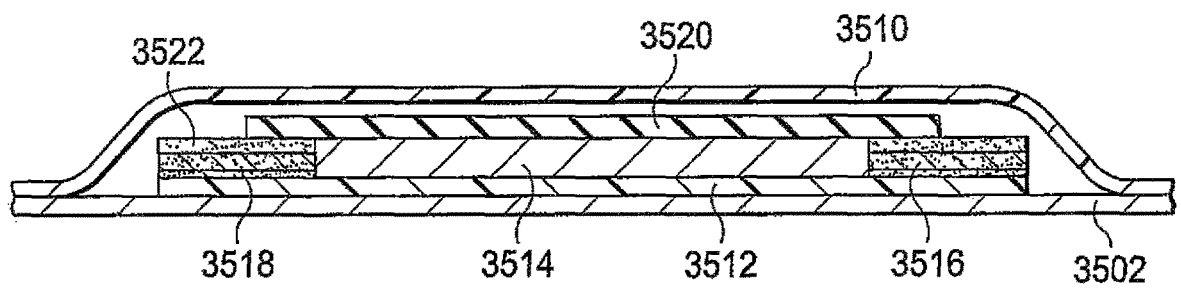
FIG. 35F illustrates a cross-sectional view of one embodiment of a multi-antigen patch.

Referring now to FIGS. 35E-F, there is illustrated the multi-antigen patch 3500 in the final stages of preparation. The multi-antigen patch 3500 has had a new peelable release liner 3510 that covers the entire multi-antigen patch 3500. The new peelable release liner 3510 may simply be applied after removing all of the liners 3508 of the patches 3504 if the antigen carriers 3506 already contain a single dose of the associated antigen. However, if the antigen carriers 3506 do not already contain antigen, then, before the new peelable release liner 3510 is applied, someone such as pharmacist may remove the covers 3420 of the patches 3504 to add a single dose of antigen at a prescribed dilutant level to the antigen carriers 3506, replace the covers 3402, and then add the new peelable release liner 3510, noting that the terminology "add a single dose of antigen" is to be interpreted as adding a sufficient amount of the associated antigen to facilitate "delivery" of a single dose of antigen. A method of adding antigen to the antigen carriers is discussed hereinbelow.

Figure 36:
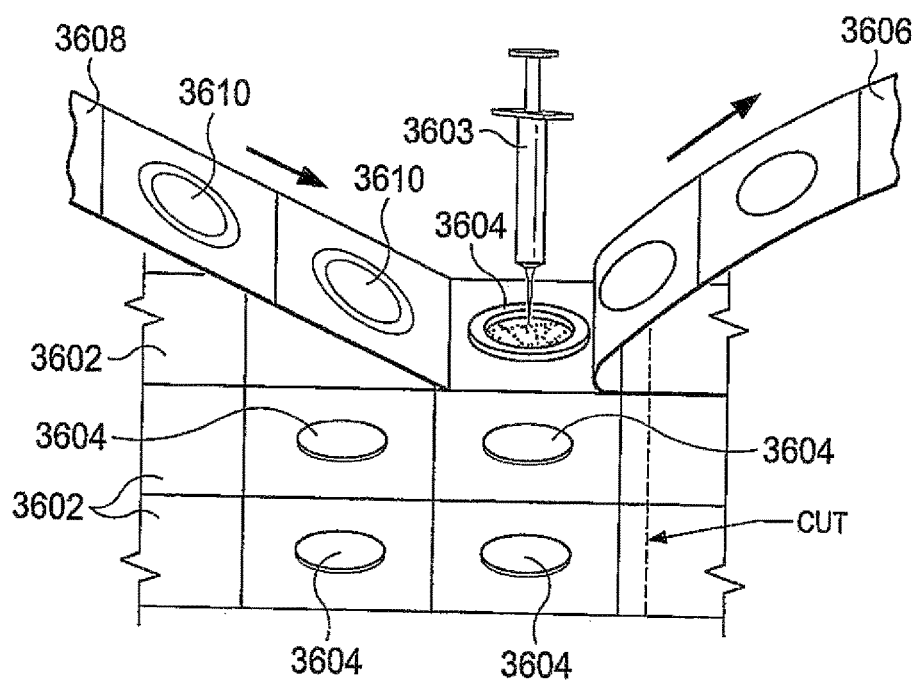
FIG. 36 illustrates one embodiment of a process for providing a single dose of antigen at a prescribed level in an antigen carrier.

Referring to FIG. 36, there is illustrated one embodiment of a process for providing a single dose of antigen at a prescribed level in an antigen carrier. It will be understood that the carrier may also contain imiquimod. There is provided a plurality of antigen patch sheets 3602, each having an antigen carrier cell 3604, the antigen carrier cell having a carrier such as a gel. The antigen patch sheets 3602 initially have disposed thereon a liner strip 3606. The liner strip 3606 is peeled away from the antigen patch sheets 3602, exposing the antigen carrier cell 3604. An antigen 3603 is then injected into the antigen carrier cell 3604. Once this is done, a peelable release liner 3608 is placed over the antigen patch sheets 3602, the peelable release liner 3608 also including a cover 3610 made of tissue, silicone, or some other porous material. The peelable release liner 3608 is applied in such a way that the cover 3610 covers the antigen carrier cell 3604. In this way, each of the antigen patch sheets 3602 may have a single dose of antigen at a prescribed dilutant level applied to each of the cells 3604 of that particular patch sheet. The antigen patch sheets 3602 may then be cut, in order to apply the antigen patches to a multi-antigen patch, such as that shown in FIGS. 35A-F.

Figure 37A:
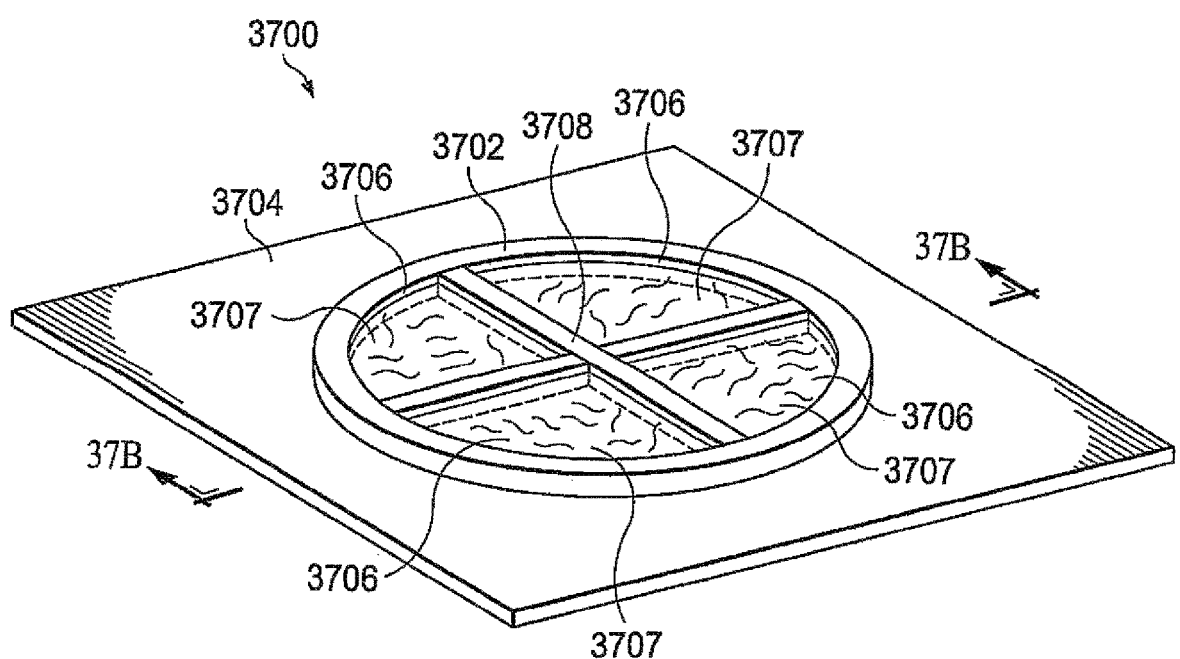
FIG. 37A illustrates a perspective view of one embodiment of a multi-antigen patch.

Referring now to FIG. 37A, there is illustrated one embodiment of a multi-antigen patch 3700. Multi-antigen patch 3700 includes a well 3702 disposed on a base 3704. The well 3702 is of a circular shape having recessed portions 3706 separated by raised cross portions 3708. The recessed portions 3706 contain a carrier gel 3707. While four recessed portions 3706 are illustrated in FIG. 37A, any number may be used.

Figure 37B:
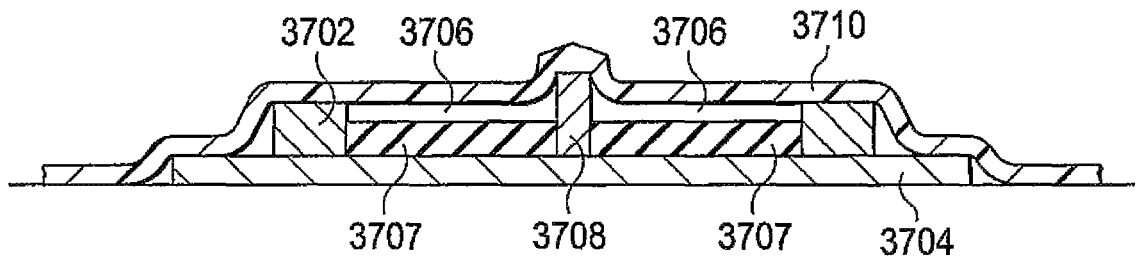
FIG. 37B illustrates a cross-sectional view of one embodiment of a multi-antigen patch.

Referring now to FIG. 37B, there is illustrated a cross-sectional view of the multi-antigen patch 3700. The multi-antigen patch 3700 has initially thereon a liner 3710 covering the base 3704 and the well 3702, in order to protect the carrier gel 3707 during activities such as shipping.

Figure 37C:
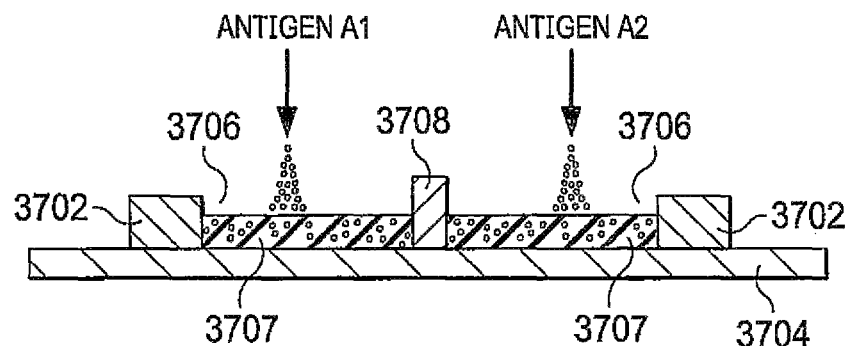
FIG. 37C illustrates a cross-sectional view of one embodiment of a multi-antigen patch after a liner is removed.

Referring now to FIG. 37C, there is illustrated another cross-sectional view of the multi-antigen patch 3700 after the liner 3710 is removed. Once the liner 3710 is removed, a single dose of antigen at a prescribed dilutant level, or multiple antigens at a prescribed dilutant level, may be inserted into the carrier gel 3707 of the recessed portions 3706 of the well 3702. This is shown in FIG. 37C where, with the liner 3710 removed, antigen A1 is inserted into the carrier gel 3707 of one of the recessed portions 3706 and antigen A2 is inserted into the carrier gel 3707 of another one of the recessed portions 3706. In this way, the carrier gel 3707 in each of the recessed portions 3706 of the well 3702 would then carry the desired amount of antigen.

Figure 37D:
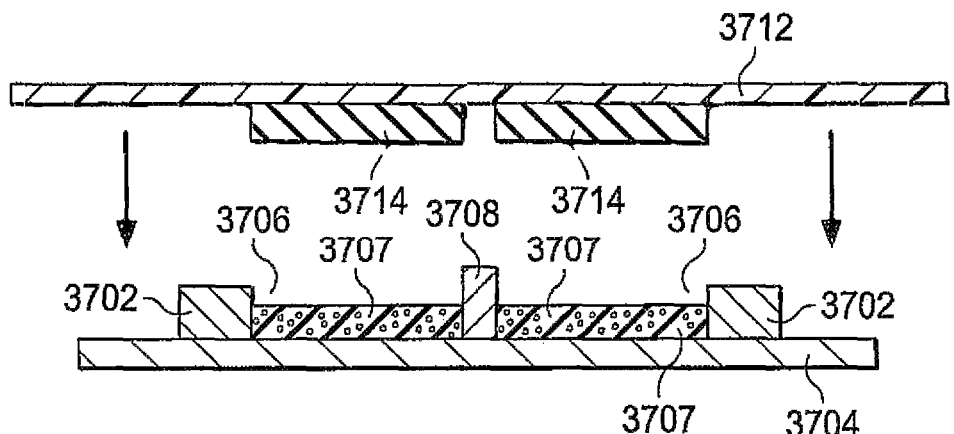
FIG. 37D and FIG. 37E illustrate a cross-section view of one embodiment of applying a peelable release liner to a multi-antigen patch.
Figure 37E:
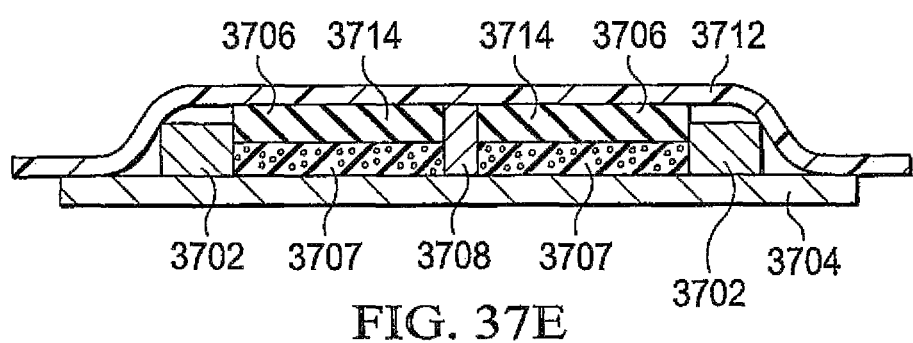

Referring now to FIG. 37D-E, there is illustrated a cross-sectional view of applying a peelable release liner 3712 to the multi-antigen patch 3700. The peelable release liner 3712 has spaced apart thereon covers 3714, one for each recessed portion 3706. When the peelable release liner 3712 is placed onto the multi-antigen patch 3700, each of the covers 3714 are inserted into or over a recessed portion 3706. The covers 3714 may be made of tissue, silicone, or some other material that allows for the antigen disposed within the gel 3707 to pass through the covers 3714 in order to come into contact with human skin. When the multi-antigen patch 3700 is to be used, the peelable release liner 3712 is removed and the covers 3714 are placed against the skin. It will be understood that, as described herein, the multi-antigen patch 3700 may be held in place on a patient's skin by an adhesive or some other means.

Figure 38:
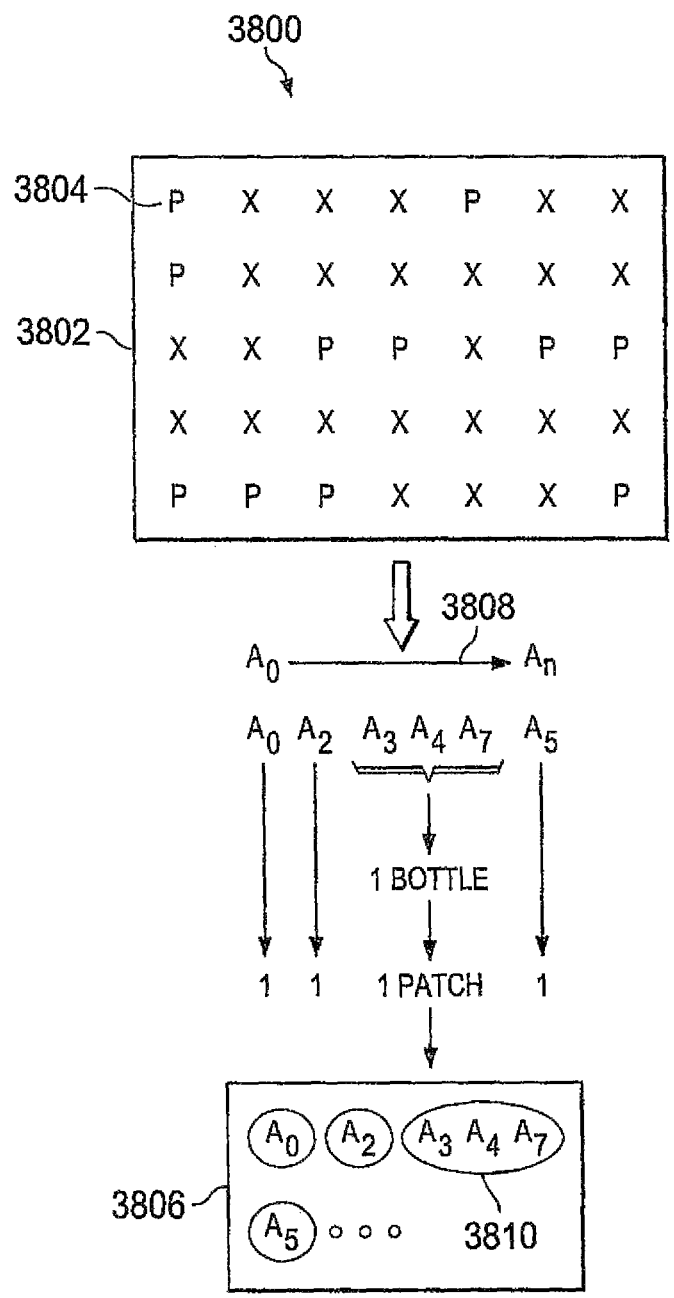
FIG. 38 illustrates one embodiment of a multi-antigen selection operation.

Referring now to FIG. 38, there is illustrated one embodiment of a multi-antigen patch antigen selection operation 3800. There is illustrated a custom patient-specific antigen results table 3802 resulting from the prick test. The table 3802 has a plurality of allergy indicators 3804, each having an allergy associated with each indicator having the letter "P" or "X," with "P" indicating a positive allergy result and "X" indicating a negative allergy result. This is used by the physician to create the script for the patient to create the patient-specific script. The results, when viewed by the medical practitioner, indicate the specific allergy reaction. For instance, the results may show that a patient is allergic to cat dander and certain types of pollen. Each of these would be marked with a "P" on the results table 3802, with an "X" marking the other allergies having a negative result. From the results table 3802, the proper antigens needed for the patient may be selected, the script generated, sent to the compounding pharmacist and applied to a multi-antigen patch 3806. If the patient is allergic to allergens $A_0$ through $A_n$, (reference number 3808), those allergens may be selected. Additionally, if certain antigens are commonly distributed as part of one antigen compound, such as a cocktail of pollen antigens, those may be applied to a single patch. This is similar to one bottle or dose of an antigen cocktail, as described herein, except provided in a patch. For example, and as illustrated in FIG. 38 (reference number 3808), if antigens $A_3$, $A_4$, and $A_7$, are typically be supplied together in the same antigen cocktail, then the multi-antigen patch 3806 may have antigens $A_3$, $A_4$, and $A_7$ within a single antigen carrier 3810.

Figure 39A:
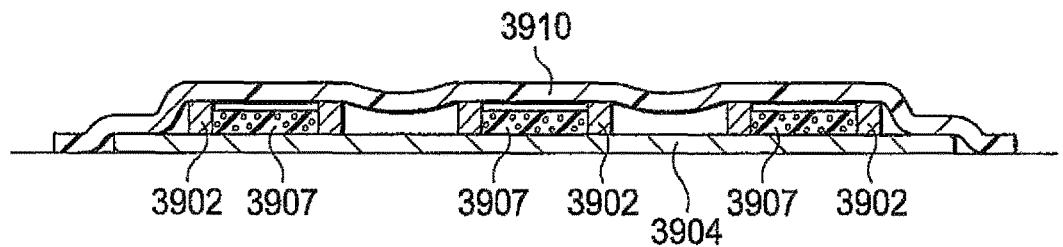
FIG. 39A illustrates a cross-sectional view of one embodiment of a multi-antigen patch.

Referring now to FIG. 39A, there is illustrated a cross-sectional view of one embodiment of a multi-antigen patch 3900. Multi-antigen patch 3900 includes wells 3902 disposed on a base 3904. The wells 3902 are of a circular shape having recessed portions containing a carrier gel 3907. Any number of wells may be present on a patch. The multi-antigen patch 3900 may initially have thereon a liner 3910 in order to protect the carrier gel 3907 during activities such as shipping.

Figure 39B:
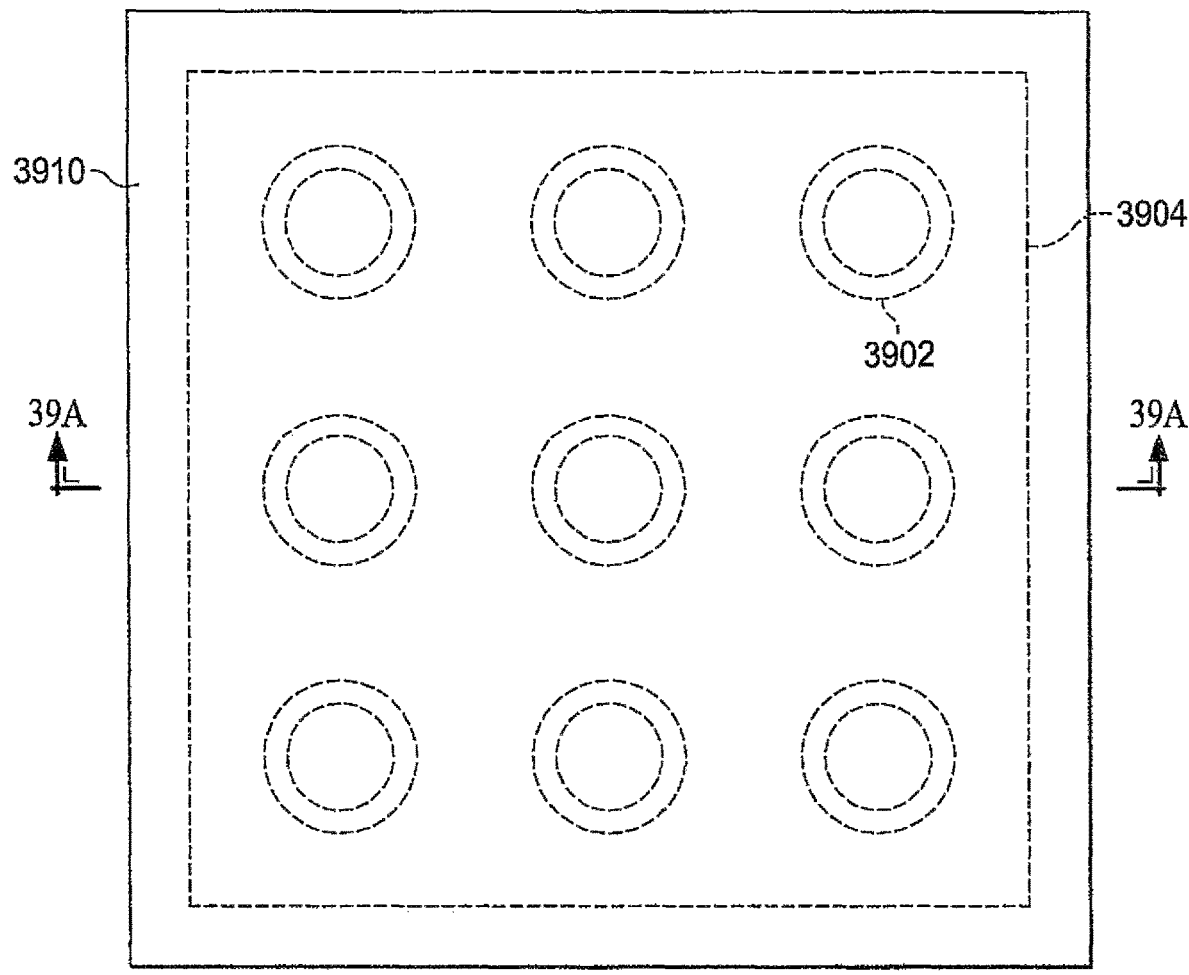
FIG. 39B illustrates a top view of one embodiment of a multi-antigen patch.

Referring now to FIG. 39B, there is illustrated a top view of the multi-antigen patch 3900. As stated, the multi-antigen patch 3900 has initially thereon a liner 3910 covering the base 3904 and the wells 3902, in order to protect the carrier gel 3907 during activities such as shipping.

Figure 39C:
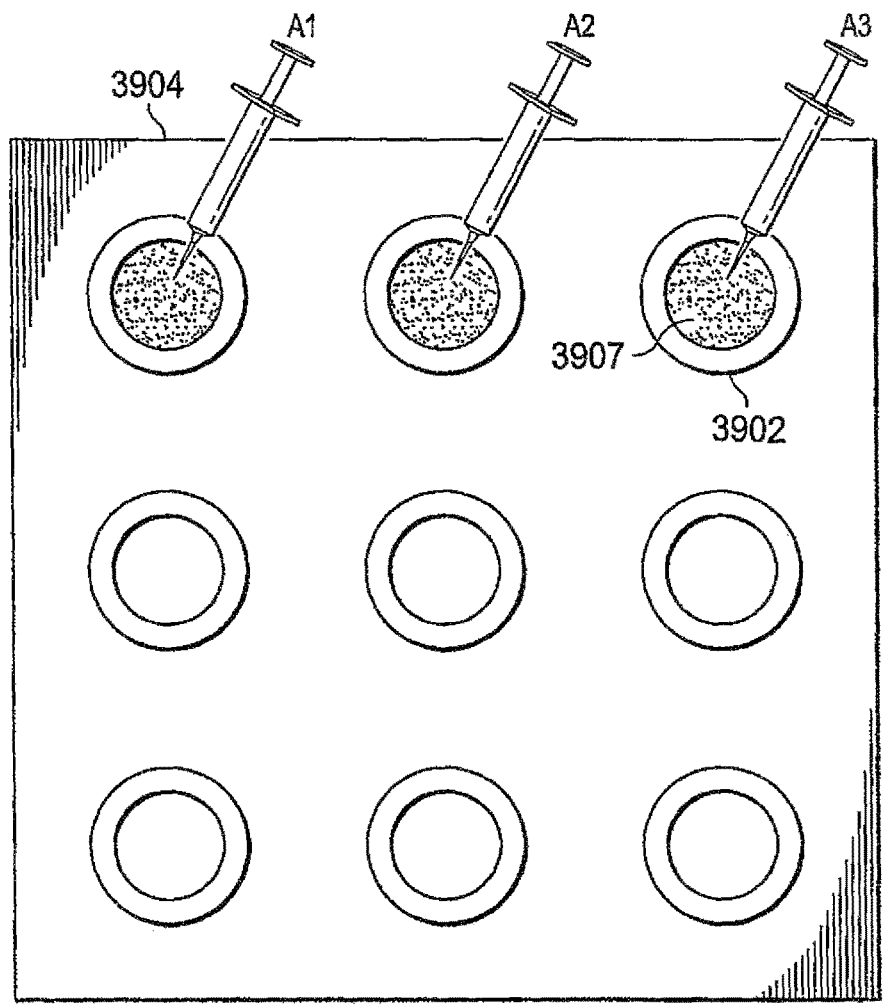
FIG. 39C illustrates a top view of one embodiment of a multi-antigen patch after a liner is removed.

Referring now to FIG. 39C, there is illustrated another top view of the multi-antigen patch 3900 after the liner 3910 is removed. Once the liner 3910 is removed, a single dose of antigen at a prescribed dilutant level, or multiple antigens at a prescribed dilutant level, may be inserted into the carrier gel 3907 in the wells 3902. This is shown in FIG. 39C where, with the liner 3910 removed, antigen A1 is inserted into the carrier gel 3907 of one of the recessed wells 3902, antigen A2 is inserted into the carrier gel 3907 of another one of the wells 3902, and antigen A3 is inserted into the carrier gel 3907 of another one of the wells 3902. This process may be repeated for each well 3702 disposed on the multi-antigen patch 3900. In this way, the carrier gel 3907 in each of wells 3902 would then carry the desired amount of antigen.

Figure 39D:
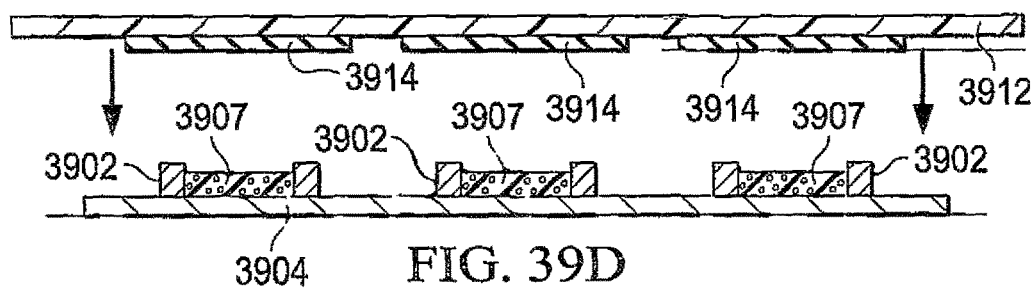
FIG. 39D and FIG. 39E illustrate a cross-section view of one embodiment of applying a peelable release liner to a multi-antigen patch.
Figure 39E:
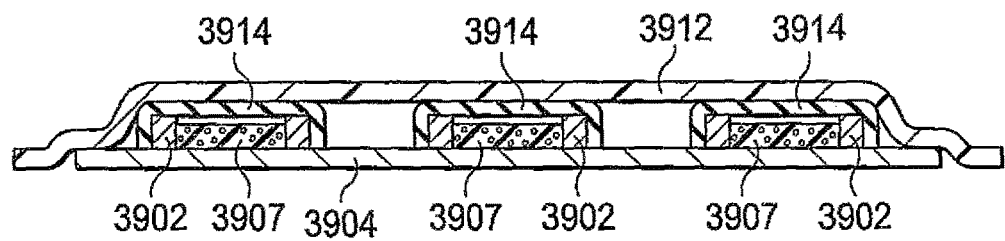

Referring now to FIG. 39D-E, there is illustrated a cross-sectional view of applying a peelable release liner 3912 to the multi-antigen patch 3900. The peelable release liner 3912 has spaced apart thereon covers 3914, one for each well 3902. When the peelable release liner 3912 is placed onto the multi-antigen patch 3900, each of the covers 3914 is inserted into or over an associated well 3902. The covers 3914 may be made of tissue, silicone, or some other material that allows for the antigen disposed within the gel 3907 to pass through the covers 3914 in order to come into contact with human skin. When the multi-antigen patch 3900 is to be used, the peelable release liner 3912 is removed and the covers 3914 are placed against the skin. It will be understood that, as described herein, the multi-antigen patch 3900 may be held in place on a patient's skin by an adhesive or some other means. This thus allows for a single dose of each antigen that is included on the patch to be transdermally delivered. Further, once the patch is created, then the pharmacist need only provide the script and the antigen base concentrate NDCs utilized, the dilution procedure and the carrier to the PBM database in order to determine the available benefits, as described in detail hereinabove.

It will be understood by one skilled in the art that variations made be made to the patch without deviating from the present inventive concept. For instance, the patch may be a single-layer drug-in-adhesive, having the drug within the adhesive layer, a multi-layer drug-in-adhesive, a matrix system patch, or rate controlled membrane patch.

It will be appreciated by those skilled in the art having the benefit of this disclosure that this method provides a customized delivery of allergen based on individual patient treatment plan. It should be understood that the drawings and detailed description herein are to be regarded in an illustrative rather than a restrictive manner, and are not intended to be limiting to the particular forms and examples disclosed. On the contrary, included are any further modifications, changes, rearrangements, substitutions, alternatives, design choices, and embodiments apparent to those of ordinary skill in the art, without departing from the spirit and scope hereof, as defined by the following claims. Thus, it is intended that the following claims be interpreted to embrace all such further modifications, changes, rearrangements, substitutions, alternatives, design choices, and embodiments.

What is claimed is:

1. A transdermal patch, comprising:
  a base;
  a plurality of wells disposed on the base in a group and spaced apart from each other, each of the wells having a bottom surface;
  a recessed portion formed in each of the wells, wherein the recessed portions each include an associated bottom recessed surface formed by the bottom surface of the associated well, an associated rim portion protruding above the associated bottom recessed surface, the associated rim portion extending upward from the associated bottom recessed surface to form an associated interior portion, the associated rim portion having a horizontal surface extending parallel to the bottom surface of the well and extending outward from each associated interior portion from an upper edge of the associated rim portion, wherein the horizontal surface of each associated rim portion has a first level and a second level, the second level higher than the first level, the second level being a top surface of a rim portion that separates one of the recessed portions from another one of the recessed portions;

a transdermal cream disposed within the interior portion of each of the recessed portions, wherein the transdermal cream includes:

an encapsulation material configured to carry immunomodulators across a dermis of a patient, wherein the encapsulation material includes a prescribed amount of one or more immunomodulators, wherein each one of the recessed portions includes a different immunomodulator, and an adhesive coating formed on a surface of the base outside a perimeter of the each of wells, wherein the adhesive coating is operable to adhere to a skin of the patient;

a release liner having a bottom surface disposed over the recessed portions; and a plurality of porous covers disposed directly below and on the release liner and each disposed within one of the recessed portions such that each of the plurality of porous covers is disposed within or over the interior portion of the respective recessed portion, wherein the plurality of porous covers each allow for the one or more immunomodulators to pass through the plurality of porous covers, wherein the bottom surface of the release liner is disposed adjacent the horizontal surface at the rim portions, such that the porous covers associated with the recessed portions and their associated wells are separated from each other by the bottom surface of the release liner.

2. The transdermal patch of claim 1, wherein the one or more immunomodulators each include an antigen or an allergen.

3. The transdermal patch of claim 1, wherein each of the recessed portions includes a single dose of the one or more immunomodulators at a prescribed diluted level.

* * * * *